United States Patent [19]
Sierks et al.

[11] Patent Number: 5,844,102
[45] Date of Patent: Dec. 1, 1998

[54] GLYCOHYDROLASE INHIBITORS, THEIR PREPARATION AND USE THEREOF

[75] Inventors: Michael R. Sierks, Baltimore, Md.; Mikael Bols, Lyngby, Denmark; Troels Skrydstrup, Orsay Cedex, France

[73] Assignee: University of Maryland Baltimore County, Baltimore, Md.

[21] Appl. No.: 301,601

[22] Filed: Sep. 7, 1994

Related U.S. Application Data

[63] Continuation-in-part of Ser. No. 271,469, Jul. 7, 1994, abandoned.

[51] Int. Cl.$^6$ .................................................. C07H 15/00
[52] U.S. Cl. ..................... 536/17.2; 536/17.3; 514/299; 514/315; 514/328; 546/116; 546/116; 546/138; 546/183; 546/220; 546/224
[58] Field of Search ................................. 536/17.2, 17.3; 514/299, 315, 328; 546/112, 116, 138, 183, 220, 242, 224

[56] References Cited

U.S. PATENT DOCUMENTS

| | | | |
|---|---|---|---|
| 3,235,541 | 2/1966 | Carlson | 260/209 |
| 4,788,335 | 11/1988 | Wagner et al. | 564/279 |
| 4,963,355 | 10/1990 | Kim et al. | 424/85.8 |
| 4,970,317 | 11/1990 | Margolin et al. | 546/112 |
| 5,156,965 | 10/1992 | Schochetman et al. | 435/188.5 |
| 5,157,116 | 10/1992 | Ducep et al. | 536/17.4 |
| 5,194,585 | 3/1993 | Paul et al. | 530/309 |
| 5,229,272 | 7/1993 | Paul et al. | 435/68.1 |

FOREIGN PATENT DOCUMENTS

| | | |
|---|---|---|
| 0 202 661 | 11/1986 | European Pat. Off. . |
| 0 389 723 | 10/1990 | European Pat. Off. . |
| 0 390 674 | 10/1990 | European Pat. Off. . |

OTHER PUBLICATIONS

Černý et al, "Synthesis with Anhydro Sugars. V. Preparation of 2,4–Di–O–Substituted 1,6–Anhydro–β–D–Hexopyranos–3–Uloses and Their Isomerization and Reduction," *Collection Czechoslov. Chem. Commun.*, vol. 33, pp. 1143–1156 (1968).

Cogoli et al, "A Probable Oxocarbonium Ion in the Reaction Mechanism of Small Intestinal Sucrase and Isomaltase," *Jnl. Biological Chem.*, vol. 250, No. 19, pp. 7802–7809 (Oct. 1975).

Dimitriadis et al, "α–Glucosidase Inhibition Improves Postprandial Hyperglycemia and Decreases Insulin Requirements in Insulin–Dependent Diabetes Mellitus," *Metabolism*, vol. 34, No. 3, pp. 261–265 (Mar. 1985).

Eis et al, "Mechanism and Synthetic Utility of Boron Trifluoride Etherate Promoted Organolithium Additions," *J. Am. Chem. Soc.*, vol. 106, No. 12, pp. 3693–3694 (1984).

Kajimoto et al, "Enzyme–Catalyzed Aldol Condensation for Asymmetric Synthesis of Azasugars, Evaluation, and Modeling of Glycosidase Inhibitors," *J. Am. Chem. Soc.*, vol. 113, No. 16, pp. 6187–6196 (1991).

Inghardt et al, "Oxirane Ring Opening of Anhydrosugars with Alkynyl–and Alkenylaluminates," *J. of Synthetic Organic Chem.*, No. 4, pp. 285–291 (Apr. 1990).

Lardinois et al, "Acarbose Treatment of Non–Insulin–Dependent Diabetes Mellitus," *Arch Intern Med*, vol. 144, pp. 345–347 (Feb. 1984).

G. Legler, "Glycoside Hydrolases: Mechanistic Information from Studies with Reversible and Irreversible Inhibitors," *Advances in Carbohydrate Chem. and Biochem.*, vol. 48, pp. 319–384, Academic Press, Inc.

Lipshutz et al, "2–Thienyl(Cyano)Copper Lithium. A Lower Order, Stable 'Cuprate in a Bottle' Precursor to Higher Order Reagents," *Tetrahedron Letters*, vol. 28, No. 9, pp. 945–948 (1987).

Papandreou et al, "Amidine, Amidrazone, and Amidoxime Derivatives of Monosaccharide Aldonolactams: Synthesis and Evaluation as Glycosidase Inhibitors," *J. Am. Chem. Soc.*, vol. 115, No. 25, pp. 11682–11690 (Dec. 1993).

Quaroni et al, "Affinity Labeling of the Active Sites in the Sucrase–Isomaltase Complex from Small Intestine," *Jnl. of Biological Chem.*, vol. 249, No. 20, pp. 6424–6433 (1974).

Reymond et al, "Antibody Catalysis of Glycosidic Bond Hydrolysis," *Angew. Chem. Int. Ed. Engl.*, vol. 30, No. 12, pp. 1711–1713 (1991).

Rhinehart et al, "Inhibition of Intestinal Disaccharidases and Suppression of Blood Glucose by a New α–Glucohydrolase Inhibitor—MDL 25,637," *Jnl. of Pharmacology and Experimental Therapeutics*, vol. 241, No. 3, pp. 915–920 (1987).

Robinson et al, "Castanospermine–Glucosides are Potent, Selective, Long–Acting Sucrase Inhibitors," *Jnl. of Pharmacology and Experimental Therapeutics*, vol. 251, No. 1, pp. 224–229 (1989).

(List continued on next page.)

*Primary Examiner*—James O. Wilson
*Attorney, Agent, or Firm*—Burns, Doane, Swecker & Mathis, L.L.P.

[57] ABSTRACT

A compound of the formula

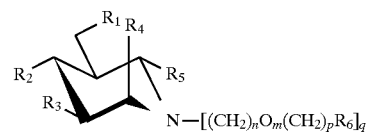

wherein n, m, and p, which may be the same or different, are a number between 0 and 5; q is a number between 0 and 10; $R_1$, $R_2$ $R_3$ $R_4$ and $R_5$, which may be the same or different, are a hydrogen, a hydroxyl, a halogen, a hydrocarbon or an O-hydrocarbon group having between 1 and 6 carbons which is aliphatic, alicyclic or aromatic, or a glycosyl group; and $R_4$ is a glycosyl group, is disclosed. Nitrogen oxides of such compounds are also included. These novel compounds have been found to be potent glycohydrolase inhibitors. Processes for preparing these novel compounds and methods for their use in the treatment of diabetes mellitus are also provided.

10 Claims, 6 Drawing Sheets

OTHER PUBLICATIONS

Robinson et al, "New Potent α–Glucohydrolase Inhibitor MDL 73945 With Long Duration of Action in Rats," *Diabetes*, vol. 40, pp. 825–830 (Jun. 1991).

W.C. Still, "Stannylation/Destannylation. Preparation of α–Alkoxy Organolithium Reagents and Synthesis of Dendrolasin Via A Carbinyl Carbanion Equivalent," *Jnl. Amer. Chem. Soc.*, vol. 100, No. 5, pp. 1481–1487 (Mar. 1978).

Winchester et al, "Amino–Sugar Glycosidase Inhibitors: Versatile Tools for Glycobiologists," *Glycobiology*, vol. 2, No. 3, pp. 199–210 (Jun. 1992).

J.B. Wright, "The Reaction of Sulfamide with α–and –62 – Diketones. The Preparation of 1,2,5–Thiadiazole 1,1–Dioxides and 1,2,6–Thiadiazine 1,1–Dioxides," *Reaction of Sulfamide with α–And β–Diketones*, vol. 29, pp. 1905–1909, (Jul. 1964).

W. Dong et al., Design of Catalytic Antibodies for Carbohydrate Synthesis, *Journal of Cellular Biochemistry*, Supplement 18D, 194, T200 (Feb. 26–Apr. 17, 1994).

T.M. Jespersen et al., "Isofagomine, a Potent, New Glycosidase Inhibitor", *Angew. Chem. Int. Ed. Engl.*, 33, No. 17, 1778–1779 (1994).

Lineweaver-Burk plot, 1/V vs 1/[S], showing competitive inhibition of β-glucosidase by the monosaccharide anolog (MB). Lines represent different inhibitor concentration.

Lineweaver-Burk plot, 1/V vs 1/[S], showing competitive inhibition of glucoamylase by the disaccharide anolog (TMJ). Lines represent different inhibitor concentration.

Plot of $K^{app}_m$ vs MB concentration for five different glycosidases. $K_i$ was calculated using the relationship $K^{app}_m = K_m(1 + [MB]/K_i)$ Plot of $K^{app}_m$ vs MB concentration for five different glycosidases. $K_i$ was calculated using the relationship $K^{app}_m = K_m(1 + [MB]/K_i)$ Plot of $K^{app}_m$ vs TMJ concentration for five different glycosidases. $K_i$ was calculated using the relationship $K^{app}_m = K_m (1 + [TMJ] / K_i)$ Plot of $K^{app}_m$ vs TMJ concentration for five different glycosidases. $K_i$ was calculated using the relationship $K^{app}_m = K_m (1 + [TMJ] / K_i)$

GLYCOHYDROLASE INHIBITORS, THEIR PREPARATION AND USE THEREOF

CROSS-REFERENCE TO RELATED APPLICATIONS

This application is a continuation-in-part of U.S. Ser. No. 08/271,469, filed Jul. 7, 1994, now abandoned, which application is hereby incorporated by reference in its entirety.

BACKGROUND OF THE INVENTION

1. Field of the Invention

This invention relates to novel sugar analogs and derivatives thereof, wherein the ring-oxygen has been replaced by a carbon, the anomeric carbon replaced with nitrogen, and the 2-hydroxy group has been removed. This invention also relates to carbohydrate analogs, wherein the anomeric nitrogen of the novel sugar analog is linked to additional sugars or derivatives thereof, and to nitrogen oxides thereof. A method of producing these analogs is also disclosed.

2. Description of the Related Art

Inhibition of intestinal glycohydrolase activity is one approach for reducing the glycemic response from dietary carbohydrate and may prove useful for the treatment of diabetes mellitus. Inhibitors of α-amylase and intestinal α-glycohydrolases represent a new class of potentially beneficial drugs for the treatment of diabetes. Puls and Keup first showed that an α-amylase inhibitor could ameliorate the glycemic response to starch (Puls et al, "Influence of an α-amylase inhibitor (Bay d 7791) on blood glucose, serum insulin and NEFA in starch loading tests in rats, dogs and man," *Diabetologie* 9:97–101 (1973)). More recently, inhibitors of intestinal α-glucohydrolases (sucrase, maltase, glucoamylase, and isomaltase) have shown similar application by reducing the glycemic response to starch and dietary disaccharides such as sucrose, and several are being clinically evaluated. Unlike the sulfonylurease, α-glucohydrolase inhibitors reduce insulin secretion and, therefore, might preserve insulin secretory capability in non-insulin-dependent diabetic subjects. Additionally, α-glucohydrolase inhibitors should not cause hyperinsulinemia, which may contribute to atherosclerosis and hypertension in patients with diabetes. Examples of such α-glucohydrolase inhibitors include acarbose and D-gluconolactone. These previously described α-glucohydrolase inhibitors, however, are readily reversible and have short durations of action.

Castanospermine is an example of an α-glucohydrolase inhibitor, which is not readily reversible and has a relatively long duration of action. Castanospermine, however, suffers from the disadvantage of not being selective for the intestinal α-glucohydrolases. It also inhibits lysosomal α-glucosidase and results in the accumulation of lysosomal glycogen. Accumulation of lysosomal glycogen has been found with the minimum effective dose required to reduce the glycemic response to sucrose (1 mg/kg). O-glucosylation of castanospermine improves selectivity for the intestinal α-glucohydrolases; however, the compounds thus produced may be susceptible to in vivo hydrolysis generating castanospermine.

Robinson et al discloses a molecule that shares structural features with some of the reversible short-acting α-glucohydrolase inhibitors (Robinson et al, "New Potent α-Glucohydrolase Inhibitor MDL 73945 With Long Duration of Action in Rats," *Diabetes* 40:825–830 (June 1991)). The molecule disclosed therein is 1,5-dideoxy-1,5-[(6-deoxy-1-O-methyl-6-α,D-glucopyranosyl)imino]-D-glucitol (MDL 73945, hereinafter referred to as "MDL"). MDL differs from other previously known α-glucohydrolase inhibitors in that the amine is linked to the C-6 of a 6-deoxyglycoside. In addition, it is a nearly irreversible inhibitor of the intestinal α-glucohydrolase inhibitor that effectively reduces the glycemic and insulin responses to a carbohydrate load in rats and monkeys. This compound was also found to have a long duration of action, most likely due to tight binding inhibition of sucrase and possibly other intestinal α-glucohydrolases, a profile that has previously been demonstrated only with castanospermine and its glucoside derivatives. In contrast to castanospermine, a dose of MDL 10-fold higher than required to reduce the glycemic response to sucrose did not affect liver lysosomal α-glucosidase activity or glycogen accumulation. This compound, however, is not reported to affect β-glucosidases or other glycohydrolases.

Many pyranoses with the ring oxygen substituted by an iminogroup are natural products and useful as potent glycosidase inhibitors (Legler, *Adv. Carbohydr. Chem. Biochem.,* 48:318 (1990)). In the last decade it has been of interest to develop effective synthesis of such compounds and their analogs for the investigation of glycosidase action and for the development of specific glycosidase inhibitors for treating metabolic disorders such as diabetes or as antiviral, antibacterial and anticancer agents (Winchester et al, *Glycobiology* 2:199 (1992)). A subject of debate is how the inhibitors interact with the enzyme. It is commonly thought that the glycosidase inhibitor should mimic the transition state in the hydrolysis of a glycosidic bond, and that in the design of new inhibitors both charge, configuration and conformation must be taken into account (Papandreou et al, *J. Am. Chem. Soc.* 115:11682 (1993); and Vasella et al). It is also commonly thought that an important feature of a good glycosidase inhibitor is the substitution of the ring oxygen with nitrogen. Recently, a catalytic antibody was developed that catalyzed the tetrahydropyranyl ether hydrolysis reaction (Reymond et al, *Angew. Chem. Int. Ed. Engl.,* 30(12):1711–1713 (1991). It can be argued that this antibody acts as a glycosidase though on an extremely simplified model. This compound is not a sugar analog. Nor was this compound reported to effectively inhibit both α and β glycosides. In the field of catalytic antibodies a transition state analog (TA) for the desired reaction is used as antigen to generate the antibodies, and in this case the antigen employed was the piperidinium-ion. With the knowledge of the composition of the usual inhibitors of glycosidases, it seemed surprising that this piperidine-derivative apparently was a TA for this simplified glycosidase model, because the nitrogen has replaced the anomeric carbon and not the ring oxygen.

With these examples in mind, it would be of interest to synthesize a monosaccharide derivative with nitrogen in place of the anomeric carbon to investigate its properties as inhibitor, particularly because no such compounds previously had been prepared.

While compounds having properties as inhibitors are of interest to the art, the ability to catalyze chemical reactions, such as the synthesis, modification or cleavage of structurally complex molecules, including proteins, nucleic acids, carbohydrates, and the like, would also be of great commercial and scientific benefit. To this end, antibodies have been prepared having catalytic activity resulting from the ability of the antibody combining site to selectively stabilize transition state analogs and to overcome entropic barriers in orienting reactants in particular reactions.

Although significant catalytic activity has been observed with such antibodies, it would also be desirable to provide catalytic antibodies and other polypeptides having enhanced catalytic activity and specificity. In particular, it would be desirable to be able to design catalytic antibodies and polypeptides having a combining site with a desired specificity and affinity for the reactant(s) of interest, which antibodies and polypeptides further provide catalytic or other reactive groups proximate the binding site. Such catalytic and reactive groups would be able to chemically participate in the reaction of interest.

SUMMARY AND OBJECTS OF THE INVENTION

In view of the above shortcomings associated with glycohydrolase inhibitors employed to date, as well as other disadvantages not specifically mentioned above, it should be apparent that there still exists a need in the art for new glycohydrolase inhibitors that are more potent and have longer duration of action than structurally similar molecules. There is also a need for inhibitors which are selective for the intestinal glycohydrolases for use as a drug for reducing postprandial hyperglycemia in both insulin-dependent and non-insulin-dependent diabetes mellitus, and for use in treating or preventing atherosclerosis and hypertension and preserving insulin secretory capability in non-insulin-dependent diabetic subjects.

Further, there is a need in the art for glycosidase inhibitors which will effectively inhibit both α- and β-glycosidases.

In addition, there is a need in the art for the development of enzymes with specific activity towards carbohydrates involved in certain disease processes, e.g., viral infection, tumor formation and tissue inflammation.

There is further a need in the art for the development of compounds having glycohydrolase activity useful for inhibition of cellulase degradation, including to inhibit the rotting of cellulosic material.

There is a still further need in the art for polypeptides having glycohydrolase activity which function as catalytic antibodies. Moreover, there is a need in the art for a method for the preparation and use of monoclonal antibodies as convenient, readily obtainable and inexpensive catalysts having a degree of specificity and efficiency of action not previously achievable in the catalytic arts.

It is, therefore, a primary object of the present invention to provide novel glycohydrolase inhibitors that are more potent and have longer duration of action than structurally similar molecules, that are selective for the intestinal glycohydrolases, and that inhibit both α- and β-glycosidases.

It is also an object of the present invention to provide pharmaceutical compositions of matter comprising an glycohydrolase inhibitor in an amount effective for reducing postprandial hyperglycemia in both insulin-dependent and non-insulin-dependent diabetes mellitus. Additionally, it is an object of the present invention to provide pharmaceutical compositions of matter comprising an glycohydrolase inhibitor in an amount effective for treating or preventing atherosclerosis and hypertension and preserving insulin secretory capability in non-insulin-dependent diabetic subjects.

It is a further object of the present invention to provide transition state analogs or inhibitors that can be used as antigens to screen for antibodies with catalytic activities, such synthetic carbohydrate analogs producing catalytic antibodies which possess specific carbohydrase activity.

It is a still further object of the present invention to provide a process for preparing novel glycohydrolase inhibitors.

In addition, it is an object of the present invention to provide a method of treating or controlling diabetes, cancer or human immunodeficiency virus (HIV).

It is a still further object of the present invention to provide glycohydrolase inhibitors useful for the prevention or inhibition of cellulase degradation or the preservation or protection of agricultural crops. Such glycohydrolase inhibitors could be used to inhibit the rotting of cellulosic material, in particular wood products. These compounds are thus useful in compositions for preserving or protecting cellulosic material, e.g., paints, stains, etc., to prevent rotting of the cellulosic material.

In addition, it is an object of the present invention to provide antibodies which catalyze a glycohydrolase reaction and function as catalytic antibodies, and methods and compositions to produce such catalytic antibodies.

It is a further object of the invention to provide a method for the preparation and use of catalytic antibodies as convenient, readily obtainable and inexpensive catalysts having a degree of specificity and efficiency of action not previously achievable in the catalytic arts.

These, and other objects of the present invention are achieved by the various aspects of the present invention.

In one aspect, the present invention relates to novel monosaccharide sugar analogs and derivatives thereof of the formula

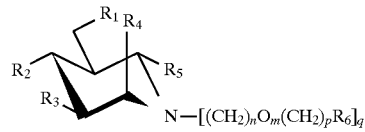

Derivatives of these compounds include compounds with any substitutions which do not eliminate its ability to bind glycohydrolase.

In a second aspect, the present invention relates to carbohydrates which include at least one sugar derivative of the formula I and at least one additional aldose or ketose, for example, any of the aldoses or ketoses well known in the art. Disaccharides are particularly preferred.

A further aspect of the present invention is a process for preparing the compounds of the present invention. These compounds are prepared by reacting a starting material of a 1,6:2,3-dianhydro-aldopyranose (e.g., 1,6:2,3-dianhydro-4-O-benzyl-β-D-mannopyranose) with a compound effective for ring-opening an epoxide group; hydrolyzing the product obtained to produce an oil which comprises a mixture of anomers; reacting the oil with an oxidizing agent in an amount effective for cleaving a carbon chain between $C_5$ and $C_6$; reacting the cleaved compound with an ammination agent in a suitable solvent under conditions suitable for ammination; and removing the protective group by a any deprotection reaction known in the art, e.g., hydrogenation, to obtain the compound of formula I, as set forth above.

A still further aspect of the present invention is a pharmaceutical composition of matter comprising the compounds of the present invention in an amount effective for inhibiting glycosidase activity, and a pharmaceutically acceptable carrier therefor.

In another aspect, the present invention relates to a method of treating or controlling diabetes, cancer or human immunodeficiency virus (HIV) comprising administering to a patient having diabetes, cancer or human immunodeficiency virus the glycohydrolase inhibitors of the present invention in an amount effective for treating or controlling diabetes, cancer or human immunodeficiency virus.

In a further aspect, the present invention relates to a method of treating or inhibiting cellulase degradation in a cellulose containing object comprising administering to the object the compounds of the present invention or compositions comprising the same in an effective amount for preventing or inhibiting cellulase degradation.

In a still further aspect, the present invention relates to a method of preserving or protecting agricultural crops comprising administering to the crop the compounds of the present invention or compositions comprising the same in an effective amount for inhibiting glycohydrolase activity in the crop.

In a further aspect, the present invention provides monoclonal antibodies which catalyze a glycohydrolase reaction and function as catalytic antibodies, and methods and compositions to produce such catalytic antibodies.

In another aspect, the present invention provides a method for the preparation and use of monoclonal antibodies which catalyze a glycohydrolase reaction for catalytically increasing the rate of a chemical reaction wherein at least one reactant is converted to at least one product.

In a still further aspect, the present invention relates to nitrogen oxides of carbohydrates which include at least one sugar derivative of the formula I and at least one additional aldose or ketose, for example, any of the aldoses or ketoses well known in the art. Disaccharide nitrogen oxides are particularly preferred.

Other objects, advantages and features of the present invention will become apparent to those skilled in the art from the following discussion.

DETAILED DESCRIPTION OF THE PREFERRED EMBODIMENTS

Figure 1A:
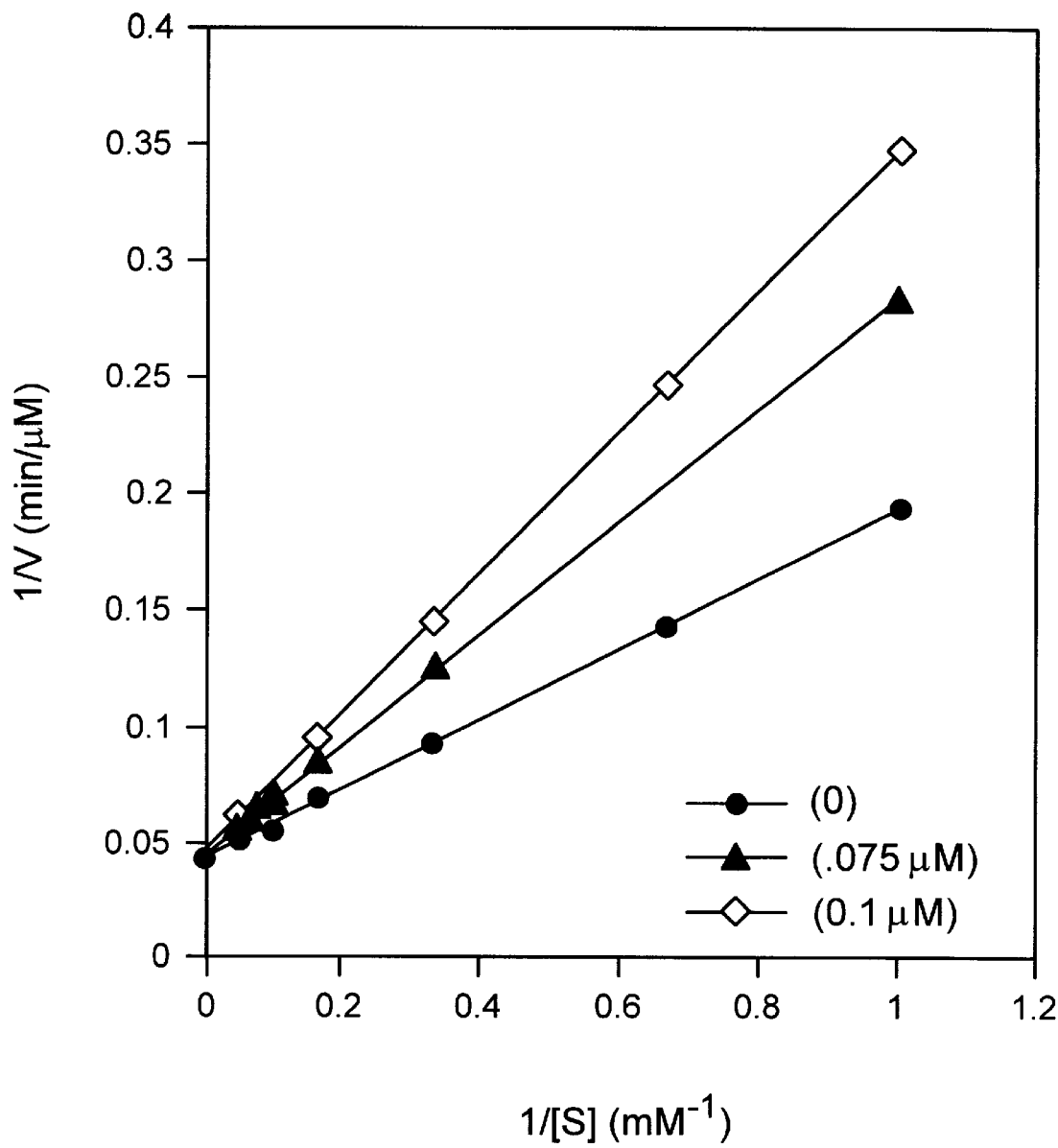
FIG. 1(a) illustrates a Lineweaver-Burk plot, 1/V vs. 1/[S], showing competitive inhibition of β-glucosidase by the monosaccharide analog (MB). The three lines represent different inhibitor concentrations as indicated.

The sugar analog of the present invention comprises a sugar analog wherein the ring-oxygen has been replaced by a carbon, the anomeric carbon replaced with nitrogen and the 2-hydroxy group has been removed. The present inventors have thus discovered a novel sugar analog and derivatives thereof of formula I as follows:

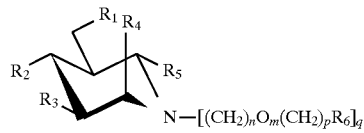

wherein n, m, and p, which may be the same or different, are a number between 0 and 5, preferably between 0 and 3, and most preferably between 0 and 2; q is a number between 0 and 10, preferably between 0 and 8, and most preferably 1; $R_1$, $R_2$, $R_3$, $R_4$ and $R_5$, which may be the same or different, are a hydrogen, a hydroxyl, a halogen atom, a hydrocarbon or an O-hydrocarbon group having between 1 and 6 carbons which is aliphatic, alicyclic or aromatic, or a glycosyl group; and $R_6$ is a glycosyl group. The glycosyl groups comprise from 1 to 3 hexose or pentose units which optionally have an ether or an acyl radical at the anomeric carbon atom of the terminal hexose or pentose unit.

The $[(CH_2)_n\, O_m\, (CH_2)_p\, R_6]_q$ group will be of a sufficient size such that the sugar analog resembles the transition state of the enzyme substrate without adversely affecting to a significant degree the ability of the analog to bind to the glycosidase.

The particular $R_1$–$R_5$ group and their stereochemical orientation may vary depending on the particular glycohydrolase desired to be inhibited. For example, an R group is employed which allows the inhibitor to more closely resemble the transition state of the enzyme substrate.

Derivatives of the sugar analog of the present invention include compounds of formula I having any substitutions which do not eliminate or significantly reduce its ability to bind glycohydrolase. For example, derivatives include compounds wherein any of the hydrogen atoms are replaced by $C_1$ to $C_3$ alkyl or alkylene groups, $C_1$ to $C_3$ alcohol groups, hydroxyl groups or halogen atoms (e.g., fluorine, chlorine, bromine, and iodine). Salts of these compounds are also included, for example, salts of inorganic acids such as hydrogen halide acids (e.g., hydrochloric acid and hydrobromic acid), sulfuric acid and phosphoric acid, salts of organic acids such as acetic acid, propionic acid, oxalic acid, malonic acid and benzoic acid, and salts of alkali metals such as lithium, sodium and potassium.

For purposes of the present invention, the compound of formula I will refer to all stereoisomers thereof, including D and L enantiomers and α and β anomers. In addition, although the $R_1$–$R_5$ groups and hydroxyl groups are shown in certain orientations, the compounds of the present invention include those wherein each of these groups are in either the equatorial or axial position.

In general, when "$R_6$" of formula I is a glycosyl group, the glycosyl group is attached either directly (n is 0) or indirectly through a $(CH_2)_n$ alkylene bridge (n is at least 1) to the ring nitrogen atom of the compound through either an exocyclic or ring carbon atom of the pentose or hexose ring. The glycosyl group may also be attached to the ring nitrogen atom by an O-glycosidic bond. A variety of position isomers for each individual glycosyl group is possible. In addition, the similar or dissimilar pentose or hexose groups of $R_6$ are linked to each other through O-glycosidic bonds wherein the bridging oxygen atom is attached to an exocyclic and/or endocyclic carbon atom of the pentose or hexose groups being linked. The glycosidic linkage are preferably either an α or β linkage and also preferably either a 1,4 or a 1,6 linkage. Again all position isomers are within the scope of the present invention. Disaccharides, wherein $R_6$ is a single pentose or hexose group and q is 1, are the particularly preferred compounds of the present invention. For example, a particularly preferred disaccharide analog of the present invention is of the formula II as follows:

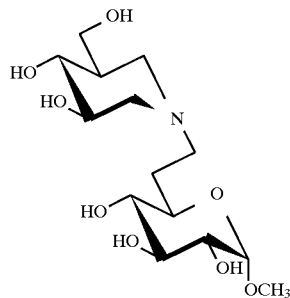

Examples of pentose and hexose groups include, for example, ribose, arabinose, xylose, lyxose, ribulose, xylulose, allose, altrose, glucose, mannose, gulose, idose, galactose, talose, psicose, fructose, sorbose, and tagatose. Preferred pentose and hexose groups include those wherein at least one hydroxyl group, preferably the C-1 hydroxyl group is substituted with an O-alkyl group, preferably a $C_1$ to $C_{10}$ O-alkyl group (e.g., methyl glucoside). All stereoisomers of these pentose and hexose groups are included within the scope of the present invention. In addition, derivatives of these pentose and hexose groups are also included, e.g., compounds of formula II having any substitutions which do not eliminate or significantly reduce its ability to bind glycohydrolase. For example, derivatives include compounds wherein any of the hydrogen atoms or hydroxyl groups are replaced by $C_1$ to $C_3$ alkyl or alkylene groups, $C_1$ to $C_3$ alcohol groups, hydroxyl groups or halogen atoms (e.g., fluorine, chlorine, bromine, and iodine). Salts of these compounds are also included.

Nitrogen oxides of the compounds of the formula I or formula II are also included in the present invention. For example, a disaccharide nitrogen oxide is of the formula III as follows:

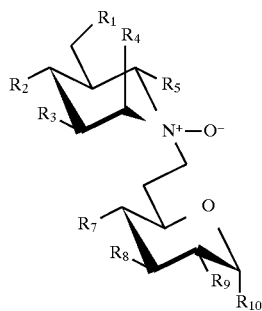

wherein $R_1$, $R_2$, $R_3$, $R_4$, $R_5$, $R_7$, $R_8$, $R_9$ and $R_{10}$, which may be the same or different, are a hydrogen, a hydroxyl, a halogen, a hydrocarbon or an O-hydrocarbon group having between 1 and 6 carbons which is aliphatic, alicyclic or aromatic, or a glycosyl group. A preferred disaccharide nitrogen oxide is as follows:

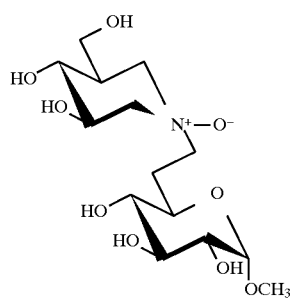

The compounds of the present invention are prepared by reacting a 1,6:2,3-dianhydro-aldopyranose which preferably comprises an art-recognized protecting group (e.g., an O-benzyl group) on the C-4 carbon, with a compound effective for ring-opening an epoxide group; followed by ozonolysis and reduction; hydrolyzing the product of (a) to obtain an oil comprising a mixture of anomers; reacting the oil with an oxidizing agent in an amount effective for cleaving a carbon chain between C-5 and C-6; reacting the cleaved compound with an ammination agent under conditions suitable for ammination; and removing the protection group by a deprotection reaction to obtain the compound of the present invention. Preferably, the compound effective for ring-opening the epoxide group is vinylmagnesium halide, alkylmagnesium halide, alkenylmagnesium halide, vinyl lithium, alkyl lithium or alkenyl lithium. In another preferred embodiment the carbon chain between C-5 and C-6 is oxidatively cleaved using an oxidation agent comprising $NaIO_4$, $HIO_4$, $KIO_4$ or $Pb(OAc)_4$. In addition, the oxidation agent is preferably present in an amount greater than stoichiometric. Suitable solvents for the ammination reaction include ethanol, methanol, propanol, butanol, pentanol, hexanol, tetrahydrofurane diethyl ether, water and dioxane. In a further preferred embodiment, the reductive ammination is carried out under hydrogen pressure in the presence of a catalyst. Preferred catalysts include palladium on charcoal, platinum, palladium, rhenium or nickel. In addition, the deprotection reaction is any deprotection reaction known in the art, preferably hydrogenation.

The compound produced according to the above process is connected to other sugars containing an appropriately positioned aldehyde or ketone group by reductive ammination. Such reactions are generally known in the art, for example, EP 0 345 104, which reference is hereby incorporated by reference. More specifically, attachment of sugars to the core compound can be carried out by reacting a compound of Formula I with a sugar aldehyde and hydrogen in the presence of palladium on carbon. In accordance with the teachings of EP 0 345 104, the compounds of Formula II can be prepared by condensing an appropriately hydroxy protected compound of the Formula I with an appropriately hydroxy protected activated glycosyl moiety, preferably using a triflate or halide, e.g., iodide, bromide and chloride, and including mesylates or tosylates or other equivalently functioning moieties appreciated by those of skill in the art. When the compound of Formula I is coupled with a triflate the reaction is effected by refluxing an admixture of equimolar quantities of the reactants in an alcohol-and water-free solvent, preferably a chlorinated solvent such as chloroform, under an inert atmosphere, preferably under nitrogen or argon, for about one to three days until the reaction is completed. Following standard procedures for the isolation and purification of the reaction products, the protecting groups are removed to obtain the desired product. Debenzylation is readily effected with standard techniques such as catalytic hydrogenation in an appropriate solvent, e.g., ethanol, using a catalyst such as palladium on carbon, or by transfer hydrogenation using cyclohexene and methanol. In those instances wherein esters were utilized (partially or completely) as the hydroxy protecting groups, it is preferred to first remove the ester group by treatment with an alkali alkoxide, e.g., sodium methoxide, in methanol to hydrolyze the esters and then deprotect the benzyl ethers using the foregoing hydrogenation procedures. In those instances wherein a glycosyl halide is coupled with the compound of Formula I the reaction is effected by heating the appropriately hydroxy protected reactants in dry dimethyl formamide (DMF) or other equivalently functioning solvent, at about 60° to 90° C. for about 12 to 36 hours, said heating taking place using excess amounts of the weak base ($K_2CO_3$) or a molecular sieve, preferably using excess molar amounts of the halide (up to three times) relative to the amine.

The nitrogen oxides of the compounds of formula I or II are prepared by methods generally known in the art, for example, by treatment with hydrogen peroxide in accordance with the procedure described in Kajimoto et al, *J. Am. Chem. Soc.* 113:6178–6196 (1991), which reference is hereby incorporated by reference. For example, hydrogen peroxide (42 mg, 50% weight solution) can be added to a 1 ml water solution containing a compound of the formula I or II (10 mg, 0.062 mmol) and the mixture then stirred at room temperature for three days. The solvent is then removed under reduced pressure to obtain the nitrogen oxide compound. Depending upon the specific compound, longer reaction time may be needed and can be easily determined by one skilled in the art. The solvent could alternatively be removed by evaporation.

The sugar analogs of the present invention have been found to be very strong inhibitors of glycosidase activity, with the compound of formula I being the most potent inhibitor reported toward β-glucosidase activity.

The compounds of the present invention block or control various glycosidase enzymes, which makes them useful for treating or controlling diabetes. For example, the compounds of formula I of the present invention have been found to be strong competitive inhibitors against glycosidases, for example, α-glucosidase, β-glucosidase, isomaltase, glucoamylase and α-mannosidase. These compounds were found to be particularly strong competitive inhibitors against β-glucosidase and glucoamylase. Surprisingly, unlike previously known glycosidase inhibitors, the compounds of the present invention were found to inhibit both α- and β-glycosidases.

Without being limited to theory, the aforesaid strong inhibition is believed to be partly due to the interaction between the compounds of the formula I and the carboxylate group that normally substitutes the anomeric carbon in the enzyme catalytic mechanism. While again not being limited to theory, the ability to inhibit both α- and β-glycosidases is believed to be due to the nitrogen at the C-1 position.

The compound of formula II and other disaccharide and oligosaccharide derivatives of the compound of formula I are also strong competitive inhibitors against glycosidases, in particular, α-glucosidase, β-glucosidase, isomaltase, glucoamylase and α-mannosidase. These compounds were found to be particularly strong competitive inhibitors against glycoamylase, comparable to the known glucoamylase inhibitor, acarbose. This compound was also found to inhibit α(β)-glucosidase to the same extent as deoxynojirimycin.

In addition, the compound of formula m and other nitrogen oxides of disaccharide and oligosaccharide derivatives of the compound of formula I or II are strong competitive inhibitors against glycosidases.

The most potent inhibitors of enzymes are transition-state analogs of enzyme substrates. The inhibitors of the present invention are chemically synthesized transition-state analogs of naturally-occurring sugar monosaccharides, disaccharides and oligosaccharides. As previously discussed, they differ in that the anomeric carbon has been replaced with a nitrogen, the C-1 hydroxyl group has been removed and the ring oxygen has been replaced with a carbon atom. As transition-state analogs, these compounds are predicted to bind tightly to the enzyme, on the basis of the theory that enzymes catalyze reactions by preferentially binding intermediates/transition states versus substrates and products. As set forth in the Examples, the inhibitory capabilities of both mono-and di-saccharide compounds of the present invention have been tested and compared against other known inhibitors, including acarbose, deoxynojirimycin and D-gluconolactone.

As a result of the ability of these transition-state analogs to tightly bind the enzyme, the compounds of the present invention may also be used to selectively identify glycosidases. As carbohydrates play an important role in many biological processes, enzymes having the ability to hydrolyze or synthesize specific carbohydrate linkages are very desirable. Phage display techniques expressing the human immunological repertoire provide a powerful means to generate antibodies having specific carbohydrase activity. Diverse libraries containing human light chain and heavy chain variable domains are constructed utilizing polymerase chain reactions (PCR) of a human B-cell lymphocyte cDNA library. A random combinational library of single chain variable domains, obtained by combining a light chain, linker DNA, and a heavy chain, is then cloned and displayed on the surface of the bacteriophage gene III minor coat protein.

Because of the strong inhibition of the compounds of the present invention to a number of different glycosidases, these analogs are useful as antigens to generate catalytic antibodies with carbohydrase activity. The compounds with low $K_d$ values may thus be used as haptens to screen the phage library for strong binders using affinity chromatography. Indeed, the inventors have found that one of the compounds of this invention, the monosaccharide (3R,4R, 5R)-3,4-dihydroxy-5-hydroxymethylpiperidine hydrochloride was shown to be a surprisingly strong inhibitor of β-glucosidase, likely due to the interaction between the monosaccharide and the carboxylate group that normally substitutes the anomeric carbon in the enzyme catalytic mechanism. The disaccharide methyl-6,7-dideoxy-7-((3R, 4R,5R)-3,4-dihydroxy-5-hydroxymethylpiperidinyl)-α-D-gluco-heptopyranoside hydrochloride showed very strong inhibition against glucoamylase. These sugar analogs in particular would thus be useful to screen a library to select catalytic antibodies.

In this regard, the nature of the forces involved in ligand binding by antibodies and substrate binding by enzymes is similar, viz., hydrogen bonding, electrostatic interaction and hydrophobic effect. The energy obtained from enzyme-substrate binding may be visualized to force electronic strain in the substrate and facilitate the formation of a transition state. There is strong evidence for the theory that enzymes bind the transition state of the reaction they catalyze better than the ground state, resulting in a reduced free energy of activation for the reaction. This has come to be known as the transition state theory of enzymatic catalysis. Other factors that may facilitate enzymatic catalysis are the proximity and orientation effects—apposition of correctly oriented reactants within the active site of the enzyme would reduce the requirement for a large number of random collisions prior to a productive reactant interaction. In principle, antibodies could catalyze chemical reactions by similar means.

Antibodies have been demonstrated to catalyze or facilitate chemical reactions, including acyl transfer, pericyclic and redox reactions. It is generally believed that these antibodies obtain their catalytic properties, like enzymes, from their ability to bind the transition state of the ligand better than the ground state.

Antibodies with enzymatic activity offer the possibility of specific, high efficiency catalytic chemical conversion of ligands. Many biological mediators are peptides or proteins, including the antigens of pathogenic organisms, hormones, neurotransmitters and tumor specific antigens. It should be possible to utilize the vast repertoire of specificities that the immune system encompasses to catalyze chemical reactions not within the scope of naturally occurring enzymes. The combination of antibody specificity with the catalytic power of enzymes has the potential of generating potent therapeutic agents. The utilization of these catalytic antibodies in medicine and industry would be greatly enhanced if a selective method of producing such catalytic antibodies were also available.

Antigen recognition by a monoclonal antibody is attributable to a specific combining site in the N-terminal region of the immunoglobulin (Ig) molecule. Ig molecules are thought to react with antigens via the same types of short range forces characteristic of 11 protein-protein interactions. Antigen-antibody interactions are highly specific because of the complementary three-dimensional shapes of the antibody's combining site and of the corresponding antigenic determinant of epitope. Such complementary shapes permit the molecules to approach each other closely and to interact over a substantial surface area. The specificity of antibody-antigen interactions is evidenced by the fact that changes in the configuration of the antigenic determinant result in marked decreases in the binding constant of the antigen to the antibody. The binding constant of an antibody for its antigen is generally much higher than that of an enzyme for its substrate.

During the course of a chemical reaction, the reactants undergo a series of transitions passing through different states until the products are reached. In molecular terms these transitions through intermediate states reflect changes in bond length, angles, etc. The transition from reactants to products may be viewed as involving formation of an intermediate which decomposes to produce the products. The overall rate of the reaction can be expressed in terms of the equilibrium constant characterizing the equilibria between the reactants, the intermediate and the products.

The preparation of catalytic antibodies against haptens that are transition state analogs is described in the following references: Pollack et al, *Science* 234:1570–1573 (1986); Pollack et al, *Cold Springs Harbor Symp. Quant. Biol.* 52–97–104; Jacobs et al, *J. Am. Chem. Soc.* 109:2174–2176; Tramontano et al, *Science* 234:1566–1570; Tramontano et al, *J. Am. Chem. Soc.* 110:2282–2286; and Janda et al, *Science* 241:1188–1191.

Using the compositions and methods of the present invention, novel catalysts and promoters are provided to enhance the rate of chemical reactions. In some cases, reactions may be catalyzed where no natural catalysts exist. The compositions and methods of the present invention are particularly suitable for the synthesis, modification, and cleavage of structurally complex molecules such as carbohydrates.

According to the present invention, polypeptides are provided which are capable of functioning as glycohydrolases promoting a chemical reaction involving the conversion of one or more reactants to one or more products. Such polypeptides include a binding site specific for at least one compound of the present invention, for example, of formula I, II or III, and an active functionality proximate the binding site which functionality is capable of chemically modifying a bound reactant. The active functionality may be provided by the side chain of an amino acid located proximate the binding site, where the side chain may be naturally-occurring or synthetic (other than naturally-occurring), or may be provided by a separate catalytic or reactive group covalently attached to an amino acid side chain. When the active functionality is a naturally-occurring amino acid side chain or a separate catalytic or reactive functionality covalently attached to a naturally-occurring amino acid side chain or a separate catalytic or reactive functionality covalently attached to a naturally-occurring amino acid side chain, the polypeptide will be other than an enzyme, usually having the structure of an antibody or an antibody fragment. When the active functionality is a synthetic amino acid side chain, the polypeptide may be any polypeptide having the desired binding site, usually having the structure of an antibody, antibody fragment, enzyme or enzyme fragment. Suitable catalytic and reactive functionalities include enzyme cofactors, metal complexes, electrophiles, nucleophiles, acidic groups, basic groups, photosynthesizers, alkylating agents, oxidizing agents, and reducing agents.

Methods for preparing catalytic polypeptides according to the present invention include both synthetic and recombinant production of polypeptides where a naturally-occurring amino acid sequence (e.g., an antibody or enzyme) is modified by the substitution and/or addition of natural and synthetic amino acids proximate the binding site, as well as post-translational modification of such polypeptides. Post-translational modification of the polypeptides may be accomplished by the covalent attachment of the active functionality to a suitable side chain of an amino acid proximate the binding site. In some cases, it will be desirable to prepare the polypeptides having a suitable amino acid for covalent linkage by recombinant techniques, typically by providing a cysteine, histidine, lysine, serine, tryptophan, or tyrosine, proximate the binding site. Alternatively, polypeptides which have not been sequenced may be modified by combining a ligand including the active functionality with the polypeptide, where the active functionality is cleavably attached to an amino acid proximate the binding site. The attachment of the active functionality to the ligand is then cleaved and the ligand removed from the polypeptide, leaving the active functionality covalently attached proximate the binding site. The active functionality may itself comprise the catalytic or reactive group of interest, or may be further selectively modified with another functionality which can act as the catalytic or reactive group of interest.

In addition to all these methods, catalytic and reactive antibodies may be prepared by eliciting them against a hapten which is a compound of the present invention, for example, of the formula I, II or III, having a particular structure which is chosen to yield catalytic antibodies which will hydrolyze a desired glycosidic bond. Such antibodies will be able to bind reactant, reactive intermediates, or transition state analogs involved in the reaction of interest. These antibodies may further comprise specifically located amino acid side chains selected to enhance the reaction rate.

In the specific embodiments, the catalytic polypeptides are prepared by first producing antibodies to the transition state analogs of the present invention, involved in the chemical reaction of interest. Conveniently, monoclonal antibody techniques and other antibody engineering technologies, for example phage display technology to generate artificial antibodies, will be utilized to obtain a source of homogenous antibodies of uniform specificity. Regarding such antibody engineering technologies, including phage display technology, see, for example, Marks et al, *Biotechnology*, 10:779–783 (1992); Marks et al, *J. Biol. Chem.*, 267:16007–16010 (1992); and Marks et al, *J. Mol. Biol.*, 222:581–597 (1991), which references are hereby incorporated by reference. Once the antibodies are obtained, they will frequently display a certain level of catalytic activity based on their ability to stabilize a transition state involved in a chemical reaction.

The catalytic antibodies produced and isolated according to the present invention have been found to have carbohydrase activity. It was surprising that such catalytic antibodies could be obtained since, prior to the present invention, catalytic antibodies having carbohydrase activity were not known. Prior to the present invention, such catalytic antibodies had not been generated and/or isolated.

The present invention further provides for the enhancement of such catalytic activity by modification of the antibody or a fragment thereof to provide an active functionality proximate the binding site defined by the antibody. The active functionality may be a naturally-occurring amino acid side chain which is positioned relative to the binding site so that it is able to interact with the transition state analog in such a way to promote the reaction rate. Alternatively, the active functionality may be a synthetic amino acid side chain or be covalently attached to the side chain of an amino acid located in the proper position relative to the antibody binding site.

Furthermore, activity and specificity of catalytic antibodies obtained according to the present invention may be improved or isolated by methods involving random mutagenesis or chain shuffling. See, for example, Jackson et al, *Proc. Natl. Acad. Sci. USA*, 88:58–62 (1991); Collet et al, *Proc. Natl. Acad. Sci. USA*, 89:10026–10030 (1992); and Marks et al, *Biotechnology*, 10:779–783 (1992).

A catalytic component of a rationally designed catalytic antibody may be obtained starting with the methods taught in U.S. Pat. No. 4,888,281. According to such processes, a plurality of monoclonal antibodies is prepared to an antigen, which is the transition state analog for the catalytic antibody. The plurality of monoclonal antibodies so generated is screened to identify a monoclonal antibody which catalyzes the reaction of interest and the monoclonal antibody which is desired to have the desired catalytic activity separated into its several component and those components screened for activity such that a catalytic component is obtained.

For example, the desired catalytic antibodies may be obtained by affinity chromatography using a column prepared with immobilized antibodies which bind compounds of the present invention, using acid shock (pH 2.7), to elute the retained protein. Identity of the fractionated material is confirmed by immunoblotting for $F_d$- and L-chains. Native polyacrylamide gel electrophoresis and silver staining on PHAST gels is conducted to confirm that the purified Fd- and L-chains are monomeric. Since antibodies and antibody fragments can be very basic, reversed polarity electrodes are used for the native PAGE, when necessary.

The present invention also relates to the use of monoclonal antibodies and other genetically engineered catalytic antibodies to catalyze chemical reactions. Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski et al, U.S. Pat. No. 4,196,265, issued Apr. 1, 1980. Methods for producing synthetic catalytic antibodies by phage display technology are set forth, for example, in Marks et al, *Biotechnology*, 10:779–783 (1992); Marks et al, *J. Biol. Chem.*, 267:16007–16010 (1992); and Marks et al, *J. Mol. Biol.*, 222:581–597 (1991).

Pharmaceutical salts of the compounds of the present invention suitable for administration by a variety of routes are known in the art and need not be described herein in detail. Examples of pharmaceutically-acceptable salts of the compounds and derivatives thereof according to the invention, include base salts, e.g., derived from an appropriate base, such as alkali metal (e.g., sodium), alkaline earth metal (e.g., magnesium), ammonium, and $NW_nH_m$ bases and salts wherein each of n and m are 0 to 4 and n+m is 4, and wherein W is a ($C_1$–$C_{18}$)alkyl. Pharmaceutically acceptable salts of an acid group or an amino group include, but are not limited to, salts of organic carboxylic acids such as acetic, lactic, tartaric, malic, isothionic, lactobionic and succinic acids; organic sulfonic acids such as methanesulfonic, ethanesulfonic, benzenesulfonic and p-toluylsulfonic acids, and inorganic acids such as hydrochloric, sulfuric, phosphoric and sulfamic acids. Pharmaceutically-acceptable salts of a compound with a hydroxy group include, but are not limited to, the anion of the compound in combination with a suitable cation such as Na+, and $NW_nH_m$, wherein W is a ($C_1$–$C_{18}$)alkyl group, and n and m are 0 to 4, and n+m is 4.

Also part of this invention is a pharmaceutical composition of matter for treating or controlling diabetes, cancer or human immunodeficiency virus comprising at least one compound of the invention described above, mixtures thereof, and/or pharmaceutical salts thereof; and a pharmaceutically-acceptable carrier therefor. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa. (1985).

For therapeutic use in a method of treating or controlling diabetes, cancer or human immunodeficiency virus a compound of the present invention or its salt can be conveniently administered in the form of a pharmaceutical composition comprising at least one of the compounds of the present invention or a salt thereof; and a pharmaceutically acceptable carrier therefor. Suitable carriers are well known in the art and vary with the desired form and mode of administration of the pharmaceutical composition. For example, they may include diluents or excipients such as fillers, binders, wetting agents, disintegrators, surface-active agents, lubricants and the like. Typically, the carrier may be a solid, liquid or vaporizable carrier, or combinations thereof. In one preferred embodiment, the composition is a therapeutic composition and the carrier is a pharmaceutically-acceptable carrier.

The compound of the invention or its salt may be formulated together with the carrier into any desired unit dosage form. Typical unit dosage forms include tablets, pills, powders, solutions, suspensions, emulsions, granules, capsules, suppositories; injectable solutions and suspensions are particularly preferred.

Each carrier must be "acceptable" in the sense of being compatible with the other ingredients in the formulation and not injurious to the patient. The carrier must be biologically acceptable and inert, i.e., it must permit the cell to conduct its metabolic reactions so that the compound of this invention may effect its inhibitory activity.

Formulations include those suitable for oral, rectal, nasal, topical (including buccal and sublingual), vaginal and parenteral (including subcutaneous, intramuscular, intravenous and intradermal) administration, with parenteral formulations being preferred.

For example, to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such as sodium chloride, glucose or glycerin can be added to make the preparations isotonic. The aqueous sterile injection solutions may further comprise oxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

The compound of the invention may be present in the composition in a broad proportion to the carrier. For instance, the compound may be present in the amount of 0.01 to 99.9 wt %, and more preferably in about 0.1 to 99 wt %. Still more preferably, the compound may be present in an amount of about 1 to 70 wt % of the composition.

The invention also provides a method of treating or controlling diabetes, cancer or human immunodeficiency virus in a patient comprising administering to a patient an effective amount of the compound or composition of this invention comprising any of the compounds of the present invention, pharmaceutically-acceptable salts thereof, or mixtures thereof.

A method of hunger or weight control is also provided by the present invention. In such a method, compounds or compositions of the present invention are administered to a patient in an amount effective for controlling hunger or weight. Without being limited to theory, the compounds of the present invention will prevent or control the breakdown of starch and carbohydrates and thus result in a "full-feeling" in the patient.

Also provided herein is a method of preserving or protecting cellulosic material by preventing or inhibiting cellulase degradation in a cellulose containing object comprising administering to the object an effective amount for preventing or inhibiting cellulase degradation of any of the compounds of the present invention or compositions comprising the same. For example, such methods are effective for inhibiting the rotting of wood products. The compounds of the present invention may, therefore, be added to any art-recognized compositions for cellulosic material, in particular wood treatment, e.g., paints, stains, sealers, etc., to prevent rotting of the cellulosic material.

Similarly, a method of preserving or protecting agricultural crops is provided comprising administering to a crop an effective amount for inhibiting glycohydrolase of any of the compounds of the present invention or compositions comprising the same. The compounds of the present invention may, therefore, be added to any art-recognized compositions for agricultural crops.

The present compounds are designed to be effective for the treatment or control of diabetes mellitus in patients including humans and other mammals. Specific types of diabetes mellitus treated include insulin-dependent diabetes mellitus, non-insulin-dependent diabetes mellitus, maturity-onset or non-insulin-dependent diabetes in the young, diabetes mellitus or carbohydrate intolerance associated with certain genetic syndromes, secondary diabetes mellitus, and gestational diabetes mellitus.

The dosage of the compound of the present invention, pharmaceutically-acceptable salts or mixtures thereof, in the compositions of the invention administered to a patient will vary depending upon several factors, including, but not limited to, the age and weight of the patient, the type of disease, e.g., diabetes, cancer or human immunodeficiency virus, treated, how advanced the disease state is, the general health of the patient, the severity of the symptoms, whether the compound of the present invention is being administered alone or in combination with other therapies or other active ingredients, the incidence of side effects and the like. The same factors should be considered when determining the dosage for hunger or weight control.

In general, a dose suitable for application in the treatment of the above-mentioned conditions is about 0.001 to 100 mg/kg body weight/dose, preferably about 0.01 to 60 mg/kg body weight/dose, and still more preferably of about 0.1 to 40 mg/kg body weight/dose per day. The desired dose may be administered as 1 to 6 or more subdoses administered at appropriate intervals throughout the day. The compounds may be administered repeatedly over a period of months or years, or it may be slowly and constantly infused to the patient. Higher and lower doses may also be administered.

The daily dose may be adjusted taking into account, for example, the above identified variety of parameters. Typically, the present compound may be administered in an amount of about 0.001 to 100 mg/kg body weight/day. However, other amounts may also be administered.

To achieve good plasma concentrations, the active compounds may be administered, for instance, by intravenous injection of an approximate 0.1 to 1% solution of the active ingredient, optionally in saline, or orally administered as a bolus.

The compound according to the invention, also referred to herein as the active ingredient, may be administered for therapy by any suitable routes, including oral, rectal, nasal, vaginal and parenteral (including intraperitoneal, subcutaneous, intramuscular, intravenous and intradermal) routes. It will be appreciated that the preferred route will vary with the condition and age of the patient, the nature of the disorder and the chosen active ingredient including other therapeutic agents. Preferred is the intravenous route.

However, other routes may also be utilized depending on the conditions of the patient and how long-lasting the treatment is.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients in a pharmaceutical composition. Other therapeutic agents suitable for use herein are any compatible drugs that are effective by the same or other mechanisms for the intended purpose, or drugs that are complementary to those of the present agents. These include agents that are effective for the treatment of diabetes mellitus, cancer or human immunodeficiency virus in humans. Examples are insulin, hypoglycemic agents such as sulfonylurease, glucagon, dextrose, diazoxide, phenytoin, thiazide diuretics and somatostatin, among others. Additional diabetes, cancer or human immunodeficiency virus therapeutic agents known in the art are also included herein.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained.

For the preservation or protection of cellulosic material, the compounds of the present invention are administered in an amount sufficient to prevent or inhibit cellulase degradation. In general, the a dose suitable for application in this method of treatment is about 0.001 to 100 mg/kg of material/ dose, preferably about 0.01 to 60 mg/kg material/dose, and still more preferably of about 0.1 to 40 mg/kg material/dose per day. The desired dose may be administered as 1 to 6 or more subdoses administered at appropriate intervals throughout the day. The compounds may be administered repeatedly over a period of months or years. Higher and lower doses may also be administered. Similar dosages and methods of administration of the compounds or compositions of the present invention are employed for the protection and preservation of agricultural crops.

In order to further illustrate the present invention and the advantages thereof, the following specific examples are given, it being understood that the same is intended only as illustrative and in nowise limitative.

EXAMPLES

Synthesis of Isofagomine. In the following examples, (3R, 4R, 4R)-3,4-Dihydroxy-5-hydroxymethyl-piperidine (Isofagomine, 1) was synthesized in a 6 step synthesis in an overall yield of 52% starting from 1,6:2,3-dianhydro-4-O-benzyl-β-D-mannopyranose (7). A hydroxymethyl group was introduced at C-2 in 7 by epoxide opening with vinylmagnesium bromide followed by ozonolysis with reductive workup to give 1,6-anhydro-4-O-benzyl-2-deoxy-2-C-hydroxymethyl-β-D-glucopyranose, (9). Hydrolysis of the anhydro bond was followed by oxidative carbon chain cleavage to give a pentodialdose, which was cyclized by reductive ammination with ammonia to give the 4-O-benzyl derivative of 1. After removing the protecting group by hydrogenation under acidic conditions 1 was isolated as its hydrochloride. This reaction scheme is as follows:

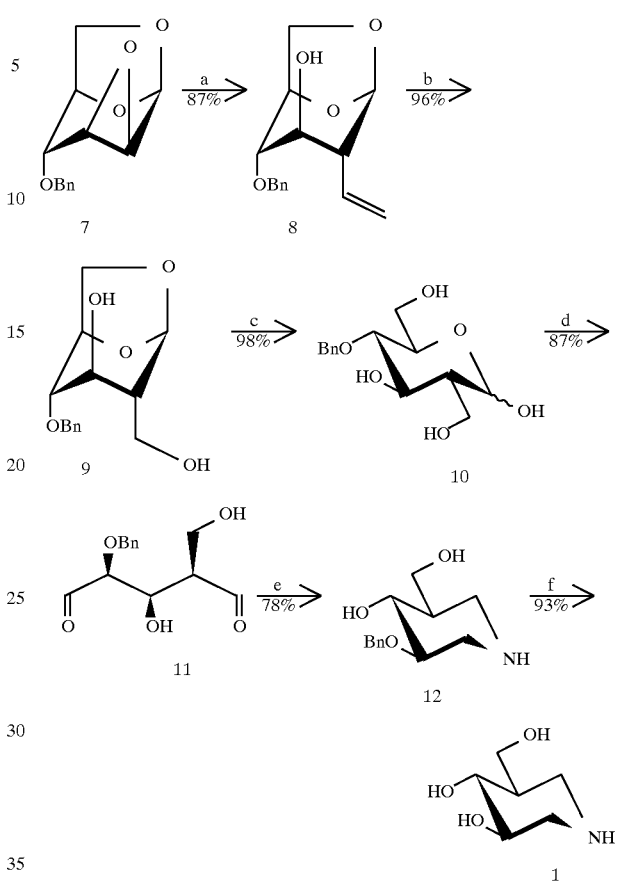

The glucose analog (3R, 4R, 5R)-3,4-dihydroxy-5-hydroxymethyl-piperidine (1) was named isofagomine since the difference between 1 and fagomine (2) is the position of the nitrogen. These two compounds as well as the previously known 1-deoxy-nojirimycin are illustrated as follows:

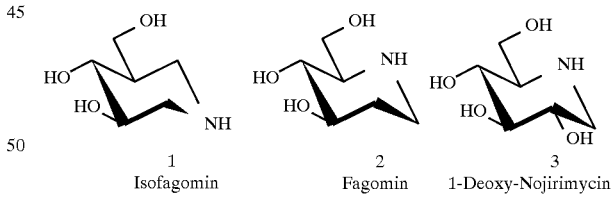

The synthesis of 1 using carbohydrates as chiral synthons in a 10 step synthesis from levoglucosan in an overall yield of 52% is described in more detail below.

The starting material 1,6:2,3-dianhydro-4-O-benzyl-β-D-mannopyranose (7) was synthesized as described by Cerny et al (Cerny et al, *J. Collection Czechoslov. Chem. Commun.* (1961), 26, 2542; and Cerny et al, *J. Collection Czechoslov. Chem. Commun.* (1968), 33, 1143) in a four step synthesis from the easily available 1,6-dianhydro-β-D-glucopyranose. (Carlson, U.S. Pat. No. 3,235,541 (1966)). To introduce a hydroxymethyl group, the epoxide was ring-opened with vinylmagnesiumbromide followed by ozonolysis of the double bond and reduction. Treatment of 7 with 10 equivalents of vinylmagnesiumbromide (Seyferth, *Org. Synthesis*, IV, 258 (1963)) gave the known compound 1,6-anhydro-4-O-benzyl-2-deoxy-2-C-vinyl-β-D-glucopyranose (Inghardt et al, *Synthesis* 285 (1990)) (8) in 87% yield. The vinylmagnesiumbromide had to be used in large excess to avoid/minimize the amount of bromohydrin byproduct. Ozonolysis of 8 followed by reductive work-up resulted in the expected compound 1,6-anhydro-4-O-benzyl-2-deoxy-2-C-hydroxymethyl-β-D-glucopyranose (9) in a 96% yield.

Hydrolysis of the anhydro bond of 9 was easily done by gentle reflux in diluted sulfuric acid. The product, 4-O-benzyl-2-deoxy-2-C-hydroxymethyl-D-glucopyranose (10), an oil containing a mixture of anomers, was obtained in quantitative yield. The β-anomer was crystallized from the oil with ethyl acetate in 27% yield. Solution of the crystalline compound resulted in mutarotation. The optical rotation rose from +32.7° to +84.4° indicating that the crystalline material was the β-anomer. This was verified by proton NMR of the freshly dissolved crystals. H-1 absorbs at 4.48 ppm as a doublet with a coupling constant of 10 Hz.

The oxidative cleavage of the carbon chain with sodium periodate was difficult as expected. It is known that periodate cleavage between C-5 and C-6 in 4-O-alkylated glucose derivatives is slow. This is because the reaction has to occur on the open chain form (Jeanloz, *Hel. Chim. Acta*, 27:1509 (1944; and Bell, *J. Chem. Soc.*, 992 (1948)). To speed up the reaction NaIO$_4$ was used in excess, and a 1:1 mixture of methanol and water was used as solvent. Use of 3 equivalents of NaIO$_4$ for 192 h at 20° C. resulted in 57% yield of the product, but when 5 equivalents NaIO$_4$ was used at 45° C. the yield of the pentadialdose was 72 to 87% after 3 h.

$^{13}$C-NMR of the product was very complex, due to several conformers and hydrates of the pentadialdose 11. To verify that the product was the expected pentodialdose, a sample was reduced with sodium borohydride, which gave the corresponding polyol.

Reductive ammination using 12M ammonia in ethanol under hydrogen pressure (3500 kPa) and using palladium on charcoal as a catalyst was expected to yield the piperidine 1. However, $^{13}$C-NMR showed two products and surprisingly both with the 4-O-benzylgroup intact. The minor compound was supposed to be the 1,5-diamine resulting from reductive ammination of both carbonyles of 11 with ammonia. This was confirmed by the fact that the amount of the byproduct could be reduced by lowering the ammonia concentration. The concentration was reduced from 12M to 0.23M which reduced the amount of the byproduct from 22% to 5%. After chromatography, the piperidine 12 was obtained in 78% yield. The benzyl group was reduced in acidic media by hydrogenation at 101 kPa with palladium as catalyst to yield the piperidine 1 as its hydrochloride, a colorless syrup, in 93%. Confirmation of the stereochemistry of 1 was based on $^1$H, decoupled $^1$H, $^{13}$C and 2D NMR spectra.

The following examples thus set forth in more detail the synthesis of isofagomine 1 from the Cerny epoxide 7. The biological activity of isofagomine 1 is also illustrated in these examples.

$^{13}$C-NMR and $^1$H-NMR spectra were recorded on Bruker instruments AC 200, AC 250 and AM 500. D$_2$O was used as solvent using DHO ($^1$H-NMR: 4.7 ppm) and acetone ($^1$H-NMR: 2.05 ppm; $^{13}$C-NNM: 29.8 ppm) as reference. With CHCl$_3$ as solvent TMS and CHCl$_3$ ($^{13}$C-NMR: 76.93 ppm) were used as references. Melting points are uncorrected. Optical rotation was measured on a Perkin Elmer 141 polarimeter. Microanalyses were carried out by Leo Microanalytical Laboratory. Concentrations were performed on a rotary evaporator at a temperature below 40° C. Dry tetrahydrofuran and ether were prepared by distillation from sodium and benzophenone. Borontrifluoroetherate was distilled (bp 124°–125° C.) and stored under argon at 5° C. and used within a week. Coppercyanide was dried under vacuum at 125° C. for 16 h. Lithium 2-thienylcyanocuprate from Aldrich was used.

Example 1

Synthesis of 1,6-anhydro-4-O-benzyl-2-deoxy-2-C-vinyl-β-D-glucopyranose, 8.

To a stirred solution of 1,6:2,3-dianhydro-4-O-benzyl-β-D-mannopyranose (7, 5.0 g, 21.3 mmol) in dry THF (25 ml), was added a solution of 1.77M vinylmagnesiumbromide 16 in THF (120.5 ml, 213 mmol). The mixture was gently refluxed for 3 h at 60° C. After cooling to room temperature a 2M NH$_4$Cl aq. solution (650 ml, pH 8) was slowly added. The aqueous layer was extracted with ethyl acetate (2×250 ml). The combined organic layers were dried (MgSO$_4$), filtered and concentrated. The crude product (4.87 g, 87%) was purified by flash chromatography using ethyl acetate/pentane 1:2 as eluent, to give 1,6-anhydro-4-O-benzyl-2-deoxy-2-C-vinyl-β-D-glucopyranose (8) as a white crystalline compound in 75.5% (4.23 g) yield. After recrystallization in ethanol: mp. 88°–91° C.; $[\alpha]_D^{20}$=−2.3° (c 4.1, CHCl$_3$) (lit$^{17}$ mp. 91°–93° C. $[\alpha]_D^{20}$=+1.2° (c 1.3, CHCl$_3$)). $^{13}$C-NMR (50 MHz, CDCl$_3$):δ135.5 (CH=), 137.7, 128.3), 127.6, 127.5 (Ph), 117.2 (CH$_2$=), 103.5 (C-1), 78.8 (C-4), 74.6 (C-3), 71.3, 70.4 (C-5, OCH$_2$Ph), 65.4 (C-6), 51.8 ppm (C-2). 1H NMR (200 MHz, CDCl$_3$): δ7.35 (d, 5H, Ph), 5.99 (m, 1H, CH=CH$_2$), 5.25 and 5.17 (s, 1H og d, 1H, CH$_2$=), 4.63) (dd, 3H, OCH$_2$Ph and H-5), 4.09 and 3.75 (d, 1H and m, 2H, H-3, H-6 and H-6'), 3.43 (s, 1H, H-4), 2.80 (broad s, 1H, OH), 2.45 (d, 1H, H-2). Anal. Calc. for C$_{15}$H$_{18}$O$_4$: C, 68.69; H, 6.92. Found: C, 68.58; H, 6.94.

Example 2

Synthesis of 1,6-anhydro-4-O-benzyl-2-deoxy-2-C-hydroxymethyl-β-D-glucopyranose, 9.

A stream of ozone (0.36 mmol/min) was passed through a solution of 1,6-anhydro-4-O-benzyl-2-deoxy-2-C-vinyl-β-D-glucopyranose (8, 3.36 g, 12.8 mmol) in ethanol (100 ml) for 43.5 minutes. The solution of the ozonide was transferred to a three-necked round bottomed flask equipped with a thermometer and a dropping funnel containing a solution of NaBH$_4$ (3.87 g, 102 mmol) in ethanol/water 1:1 (35 ml). The solution of NaBH$_4$ was added dropwise in such a manner to keep the temperature below 20° C. (cooling on ice bath). After stirring for 45 min Amberlite IR 120, H$^+$ (100 ml) was added. After stirring for another 30 minutes, the ion exchange resin was filtered off and rinsed with water. The solution was evaporated and co-concentrated with methanol (3×80 ml). The residue was a colorless syrup obtained in 96% (3.28 g) yield. This syrup was flash chromatographed using ethyl acetate/pentane 2:1 and ethyl acetate as eluent to give 9 in a 63% (2.14 g) yield as a crystalline compound. In some runs the crude syrup crystallized and was recrystallized from chloroform: mp. 111°–113°; $[\alpha]_D^{20}$=41.4° (c; 2.05, CH$_3$OH). $^{13}$C-NMR (50 MHz, D$_2$O):δ139, 130.1, 129.8 (Ph); 102.0 (C-1);, 80.5 (C-4), 76.1 (C-3), 72.9 (OCH$_2$Ph), 67.4 (C-5), 66.2 (C-6), 61.7 (C-2'), 49.0 ppm (C-2). Anal. Calc. for C$_{14}$H$_{18}$O$_5$: C, 63.15; H, 6.81. Found: C, 63.14; H, 6.79.

Example 3

Synthesis of 4-O-benzyl-2-deoxy-2-C-hydroxymethyl-D-glucopyranose, 10.

1,6-Anhydro-4-O-benzyl-2-deoxy-2-C-hydroxymethyl-β-D-glucopyranose (9, 1.59 g, 6.0 mmol) was dissolved in 1M sulfuric acid (30 ml) by heating to reflux. The anhydride was refluxed for 1 h. After cooling to room temperature the solution was poured through a column containing Amberlite IR 67, OH⁻ (120 ml). The column was rinsed with water followed by methanol (400 ml). The eluated liquid was concentrated. The residue was a colorless syrup obtained in 98% (1.67 g) yield. Flash chromatography using ethyl acetate and ethyl acetate/methanol 10:1 as eluent gave the product in 76% (1.29 g) yield. One of the anomers (β) could be obtained by crystallization in ethyl acetate in 27% yield as a white crystalline compound. mp. 102°–105° C., $[\alpha]_D^{20}$= +32.7°→84.4° (c 1.0, $CH_3OH$). $^{13}C$-NMR (50 MHz, $D_2O$):δ136.8, 128.3, 128.0 (Ph), 94.1 (C-1, β), 91.4 (C-1, α, 78.6 (C-4), 74.4 (C-3), 70.3 ($OCH_2Ph$, C-6 β), 69.5 (C-6, β), 60.3 (C-5), 59.1 (C-2', α), 56.6 (C-2', β), 47.7 ppm (C-2, α). $^1H$-NMR (200 MHz, $D_2O$), 5.13, (d, 1H, H-1 (α), $J_{1,2}$=3.5 Hz), 4.48 (d, 1H, H-1 (β), $J_{1,2}$=10 Hz). Anal. Calc. for $C_{14}H_{20}O_6$×0.3 $H_2O$: C, 58.04; H, 7.17. Found: C, 58.07; H, 7.19.

Example 4

Synthesis of 4-O-benzyl-2-deoxy-2-C-hydroxymethyl-D-xylo-pentodialdose, 11.

To a solution of 4-O-benzyl-2-deoxy-2-C-hydroxymethyl-D-glucopyranose 10 (1.41 g, 5.0 mmol) in methanol (15 ml) was added a solution of sodium periodate (5.35 g, 25.0 mmol) in water (50 ml), dropwise over 15 minutes. Further methanol (25 ml) was added. The mixture was stirred at 45° C. for 3 h. The precipitated iodate was filtered off, and the mixture was concentrated. By solution of the residue in ethyl acetate/ethanol 1:1 (80 ml), more iodate was precipitated and filtered off. The mother liquour was concentrated and the residue (2.07 g) was flash chromatographed using ethyl acetate as eluent. The purified product was obtained as a yellow syrup in 87% (1.09 g) yield and 9% of unreacted starting material (0.13 g) was isolated. The purified product was used immediately in the next reaction. $^{13}C$-NMR was complex and the product was identified as the reduced polyol. To a solution of 11 (0.16 g, 0.76 mmol) in ethanol/water 1:1 (4 ml), $NaBH_4$ (0.21 g, 5.6 mmol) in ethanol/water 1:1 (8 ml) was added dropwise in such a manner to keep the temperature below 10° C. The reaction mixture was stirred for 45 min at room temperature. Amberlite IR 120, H⁺ (6 ml) was added. After stirring for 30 min the Amberlite was filtered off and rinsed with water and ethanol. The mother liquour was concentrated and co-concentrated with methanol (3×6 ml). $^{13}C$-NMR (50 MHz, $D_2O$):δ140.0, 131.1, 130.7 (Ph); 82.0 (C-4); 75.0 ($OCH_2Ph$); 71.8 (C-3); 62.9, 61.6 (C-1, C-2, C-5); 46.6 ppm (C-2). $^1H$ NMR (200 MHz, $D_2O$):δ7.45 (s, 5H, Ph); 4.70 (2 d, 2H, $OCH_2Ph$); 3.87 (k, 1H); 3.82 (d, 2H); 3.78 (t, 1H); 3.69 (k, 2H); 3.58 (dd, 2H); 1.95 ppm (sext, 1H, H-1). MS (CI, $NH_3$): m/z 257 (M+H⁺), 274 (M+$NH_4^+$).

Example 5

Synthesis of (3R,4R,5R)-3-benzyloxy-4-hydroxy-5-hydroxymethyl-piperidine, 12.

To a solution of 4-O-benzyl-2-deoxy-2-C-hydroxymethyl-D-xylo-pentodialdose (11, 1.77 g) in ethanol (40 ml) was added 0.29M $NH_3$ in ethanol (162 ml) and 5% palladium on charcoal (300 mg). The mixture was hydrogenated at 3500 kPa at 20° for 15 h. The reaction mixture was filtrated and concentrated. The residue (1.85 g) was flash chromatographed using ethanol/$NH_4OH$ (25% aq)/triethylamine 122:2:1 as eluent giving the product as a colorless syrup (getting colored after storing) in 78% yield. $[\alpha]_D^{20}$ =+13.5° (c; 1.0, EtOH). $^{13}C$-NMR (62.9 MHz, $D_2O$):δ138.1, 128.1, 127.3 (Ph); 80.6 (C-3), 74.9 (C-4); 71.8 ($OCH_2Ph$); 62.5 (C-5'); 48.0 (C-2); 46.8 (C-6); 45.0 ppm (C-5). $^1H$-NMR (500 MHz, $D_2O$):δ7.3 (s, 5H, Ph); 4.65, 4.51 (2 d, 2H, $OCH_2Ph$, $J_{gem}$=12 Hz); 3.66 (dd, 1H, H-5a', $J_{5a',5b'}$=10 Hz, $J_{5a',5}$=5.5); 3.57 (dd, 1H, H-5'b, $J_{5a',5b'}$=10 Hz, $J_{5b',5}$=4.5); 3.41 (dd, 1H, H-4, $J_{3,4}$=11 Hz, $J_{4,5}$=9 Hz); 3.3 (broad, N-H); 3.27 (dd, 1H, H-3, $J_{3,2zx}$=11 Hz, $J_{3,2eq}$=4 Hz); 3.22 (dd, 1H, H-2eq, $J_{2eq,2ax}$=11, $J_{eq,3}$=4 Hz); 2.97 (dd, 1H, H-6 eq, $J_{6eq,6ax}$=12 Hz, $J_{6eq,5}$=4 Hz); 2.38 (t, 1H, H-2ax, $J_{2ax,2eq}$=$J_{2ax,3}$=11 Hz); 2.31 (t, 1H, H-6ax, $J_{6ax,6eq}$=$J_{6ax,5}$=12 Hz); 1.80 ppm (m, 1H, H-5). MS (CI, $NH_3$): m/z 238 (M+H⁺).

Example 6

Synthesis of (3R,4R,5R)-3,4-dihydroxy-5-hydroxymethyl-piperidine hydrochloride, 1.

(3R, 4R, 5R)-3-Benzyloxy-4-hydroxy-5-hydroxymethyl-piperidine, (12, 0.527 g, 2.2. mmol) was dissolved in 0.5M HCl (5.3 ml) and ethanol,(50 ml), 5% palladium charcoal (300 mg) was added. The mixture was hydrogenated at 101 kPa and 20° C. for 18 h. The reaction mixture was filtrated and concentrated to give the product in 93% (0.375 g) yield. $^{13}C$-NMR (50 MHz, $D_2O$):δ70.7 and 68.1 (C-3 and C-4); 58.6 (C-5'); 46.2 and 44.4 (C-2 and C-6); 40.6 (C-5). $^1H$-NMR (500 MHz, $D_2O$, PH<1, ref. HOD 4.63 ppm):δ3.72 (dd, 1H, H-5b', $J_{5a',5b'}$=11.5, $J_{5,5b'}$=3.3 Hz); 3.67 (ddd, 1H, H-3, $J_{3,2ax}$=11.2, $J_{3,4}$=8.9, $J_{3,2eq}$=4.9 Hz); 3.64 (dd, 1H, H-5a', $J_{5a',5b'}$=11.5, $J_{5,5b'}$=6.2 Hz); 3.43 (ddd, 1H, H-2eq, $J_{2eq,2ax}$=12.7, $J_{2eq,3}$=4.9. $J_{2eq,6eq}$=2.0); 3.42 (dd, 1H, H-4, $J_{4,5}$=10.5, $J_{4,3}$=8.9 (Hz); 3.41 (ddd, 1H, H-6eq, $J_{6eq,6ax}$=13.4, $J_{6eq,5}$=3.8, $J_{6eq,2eq}$=2.0 Hz); 2.87, 12.7, $J_{2ax,3}$=11.2 Hz); 1.86 ppm (ddddd, 1H, H-5). If necessary the piperidine could be chromatographed using ethanol/$NH_4OH$ (25% aq) 10:1 to give the free piperidine $[\alpha]_D^{20}$=+19.6° (c 0.85, EtOH). MS (CI, $NH_3$): m/z 148 (M+H⁺). Anal. Calc. for $C_6H_{13}NO_3$: C,48.97; H, 8.90; N, 9.52. Found: C, 48.46; H, 9.33; N, 9.17.

Example 7

The enzymes α-glucosidase (yeast), β-glucosidase (almonds), isomaltase (bakers yeast) and α-mannosidase (jackbean) were purchased from Sigma Chemical Company. Glucoamylase was isolated by the present inventors by expressing the gene from Aspergillus awamori in yeast, by methods well known in the art. Enzyme assays were performed by using p-nitrophenol -α (or β)-glucopyranosides as substrate at 37° C. in phosphate buffer (0.05M, pH 6.8) for α (β)-glucosidase and isomaltase, and p-nitrophenol-α-mannopyranoside as substrate at 25° C. in citrate (0.05M, pH 4.5) buffer for α-mannosidase. Glucoamylase was assayed using maltose as substrate at 50° C. in sodium acetate buffer (0.05M, pH 4.5).

Figure 1B:
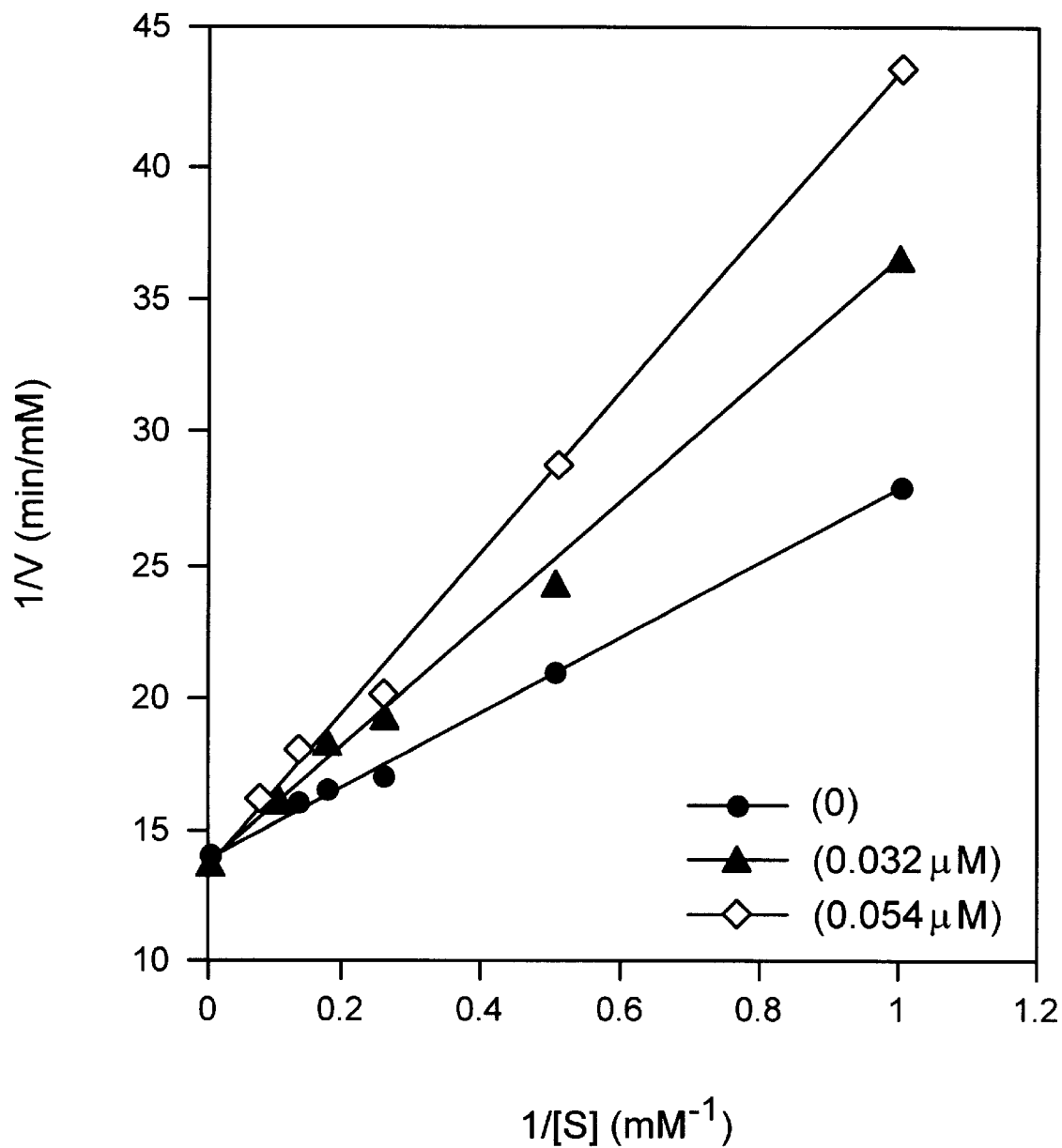
FIG. 1(b) illustrates a Lineweaver-Burk plot, 1/V vs. 1/[S], showing competitive inhibition of glucoamylase by the disaccharide analog (TMJ). The three lines represent different inhibitor concentrations as indicated.

FIG. 1(a) illustrates a Lineweaver-Burk plot, 1/V vs 1/[s], showing competitive inhibition of β-glucosidase by isofagomin at different inhibitor concentrations. FIG. 1(b) illustrates a similar Lineweaver-Burk plot, 1/V vs 1/[s], showing competitive inhibition of glycoamylase by the disaccharide analog of formula II at different concentrations.

Figures 1, 2A:
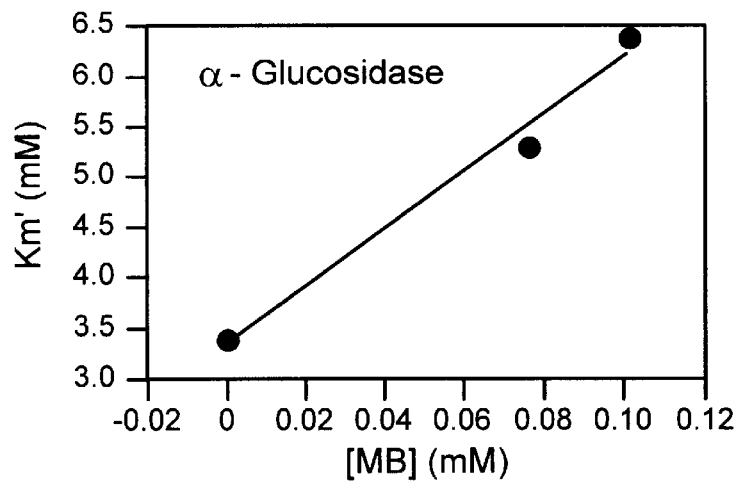
FIG. 2(a) represents a plot of $K^{app}_m$ vs concentration of the monosaccharide analog (MB) for five different glycosidases. $K_i$ was calculated using the relationship $K^{app}_m = K_m(1+[MB]/K_i)$.
Figures 2, 2A:
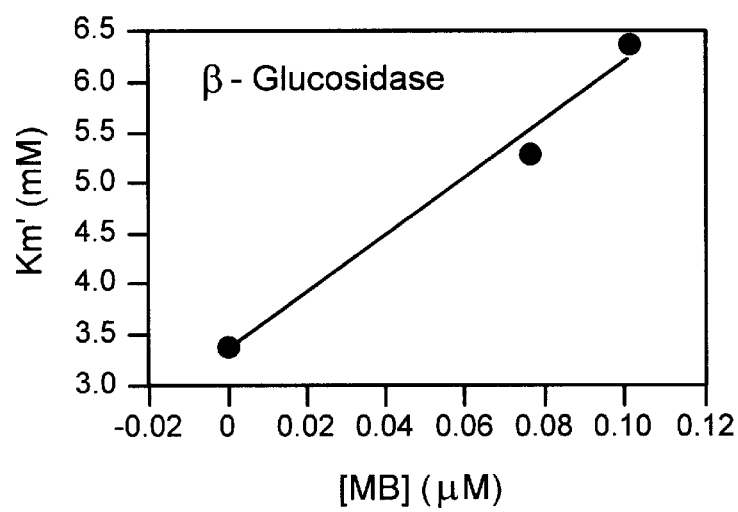
Figures 2, 2A, 3:
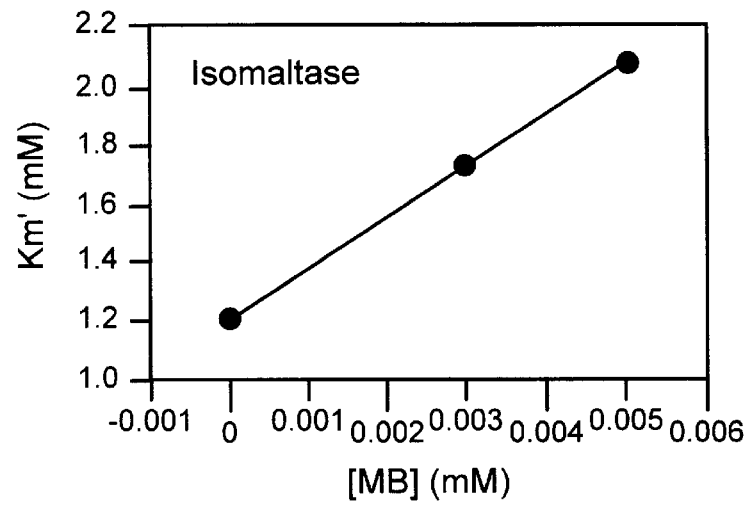
Figures 2, 2A, 3, 4:
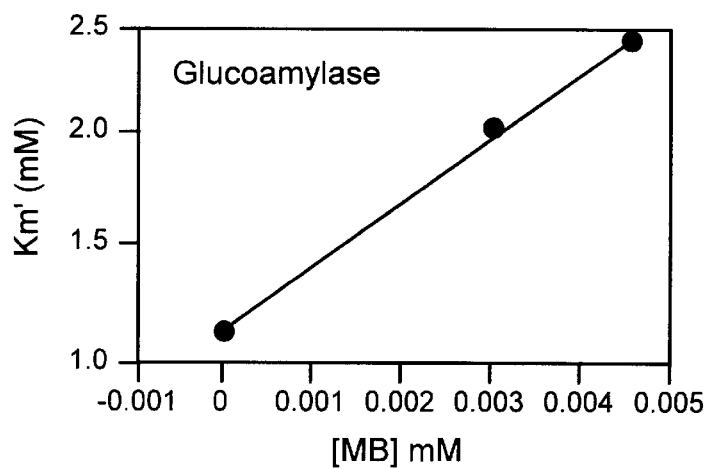
Figures 2, 2A, 3, 4, 5:
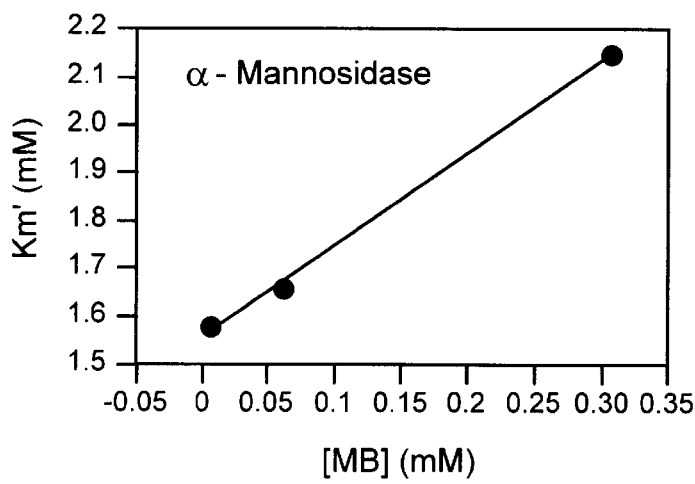
Figures 1, 2B:
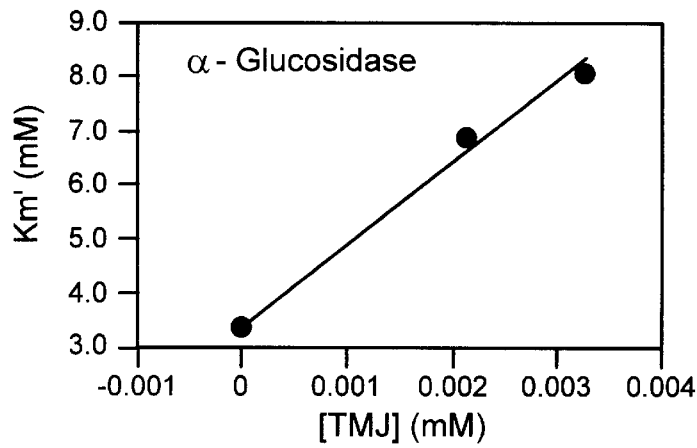
FIG. 2(b) represents a plot of $K^{app}_m$ vs concentration of the disaccharide analog (TMJ) for five different glycosidases. $K_i$ was calculated using the relationship $K^{app}_m = K_m(1+[MB]/K_i)$.
Figures 2, 2B:
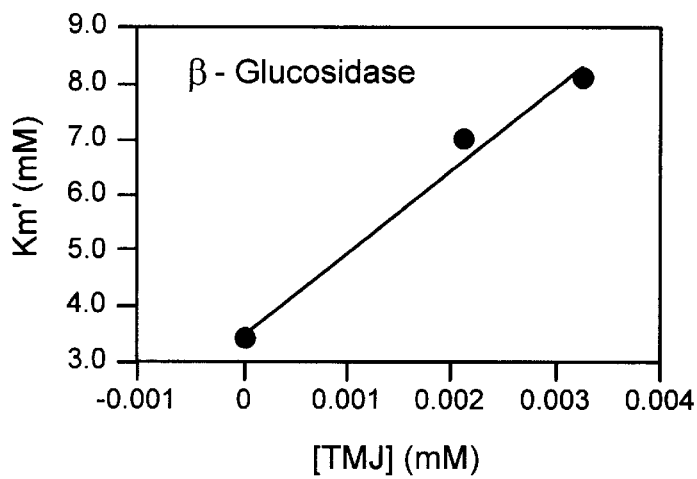
Figures 2, 2B, 3:
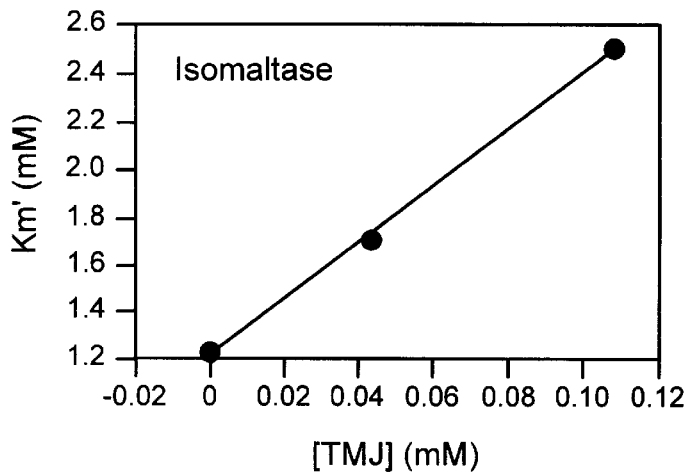
Figures 2, 2B, 3, 4:
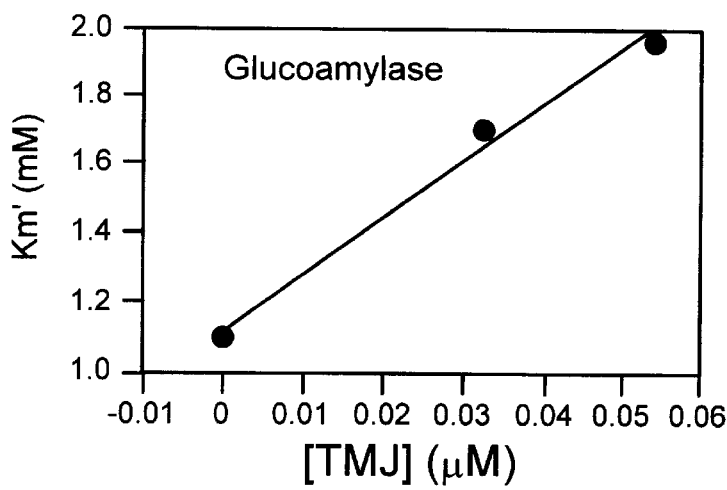
Figures 2, 2B, 3, 4, 5:
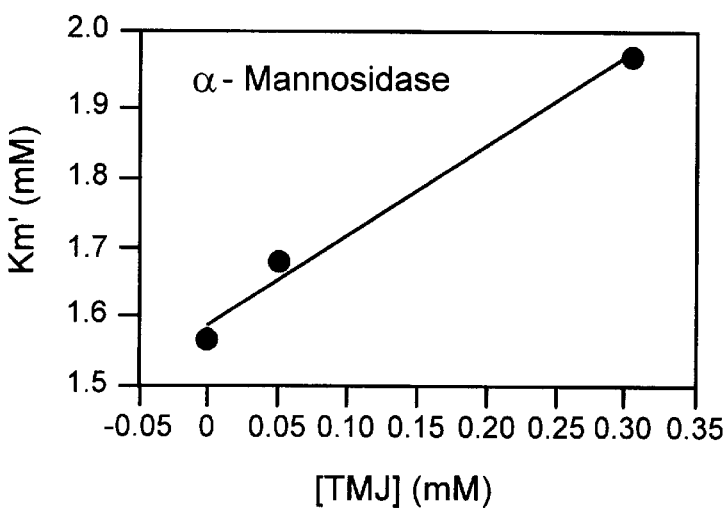

Michaelis-Menten constant, $K_m$, was calculated using software Grafit (Erithacus Software Ltd.). $K_i$ was calculated by plotting $K^{app}_m$ vs. [Inhibitor]. FIG. 2(a) represents a plot of $K^{app}_m$ vs. [Inhibitor], wherein the inhibitor is the monosaccharide sugar analog isofagomin, obtained for five different glycosidases. FIG. 2(b) represents a similar plot of $K^{app}_m$ vs. [Inhibitor], wherein the inhibitor is the disaccharide sugar analog of formula II, obtained for five different glycosidases.

The particular inhibition constants obtained using the above described method were as follows (units of $K_i$ are μM):

| Enzyme | Acarbose | Deoxy-nojirimycin | Deoxyman nojirimycin | MB | TMJ |
|---|---|---|---|---|---|
| α-Glucosidase | 81.5 | 25.4 | (>$10^{-3}$M) | 85.9 | 58.8 |
| β-Glucosidase | (10 > −4M) | 47.5 | 304 | 0.11 | 2.3 |
| Isomaltase | (10 > −4M) | 11.2 | 49.3 | 7.2 | 103 |
| Glucoamylase | 0.024 | 9.8 | 66 | 3.7 | 0.063 |
| α-Mannosidase | 7600 | 275 | 278 | 775 | 1230 |

From the above table of inhibition constants, it can thus be seen that the compounds of the present invention provide strong inhibitors for various glycosidases. The monosaccharide analog is a particularly strong inhibitor of β-glucosidase, while the disaccharide analog is a particularly strong inhibitor of glucoamylase.

Example 8

A wood treatment composition containing approximately 10 mg/kg of wood per day of isofagomin is administered to a piece of wood. After several months of treatment, the piece of wood is analyzed. No cellulase degradation is detected.

Example 9

A composition for treating agricultural crops containing approximately 10 mg/kg of crop per day of isofagomin is administered to a crop. After several months of treatment, the crop is analyzed. No glycohydrolase degradation is detected.

Example 10

The monoclonal antibodies useful in the present invention are prepared by modification of the technique disclosed by Koprowski et al in U.S. Pat. No. 4,196,265, issued Apr. 1, 1980, which is hereby incorporated by reference. The details of that process are well known to those of ordinary skill in the art. In one embodiment of this invention, a series of monoclonal antibodies directed to the reactant are prepared under suitable conditions. This involves first immunizing BALB/C mice with isofagomin as the antigen. Antibody producing lymphocytes are then removed from the spleens of the immunized mice and hybridized with myeloma cells such as SP2/0 cells to produce hybridoma cells.

These hybridoma cells are then plated in the wells of microtiter plates. The series of monoclonal antibodies being produced by the hybridoma cells is screened under appropriate conditions to identify monoclonal antibodies which have glycohydrolase activity under appropriate conditions. Screening is conveniently accomplished by treating a standardized solution of the reactant with an aliquot of medium withdrawn from a reactant with an aliquot of medium withdrawn from a microtiter well and measuring the presence of the desired product by conventional instrumental methods. The measurement is readily conducted, for example, by spectrophotometric methods or by gas-liquid or high pressure liquid chromatography. By comparison with standardized samples of the desired product or reactant, rates of reaction are quantified. In this manner, wells containing hybridoma cells producing catalytic monoclonal antibodies are identified. The selected hybridoma cells are then cultured to yield colonies.

These colonies may be further propagated in in vitro or in vivo systems. In the latter case, mice such as syngeneic BALB/C mice are inoculated intraperitoneally with the selected hybridoma cells and produce tumors, generally within two or three weeks. These tumors are accompanied by the production of ascites fluid which contains the desired monoclonal antibodies. The monoclonal antibodies are then separately recovered from the ascites fluid by conventional methods such as ultrafiltration, ultracentrifugation, dialysis and immunoaffinity chromatography.

In accordance with this invention the separately recovered monoclonal antibodies are contacted with the reactant under suitable conditions permitting the formation of a complex between the monoclonal antibody and the reactant. Those of ordinary skill in the art will appreciate that the conditions suitable for complex formation may vary depending on the particular reactant and the monoclonal antibody under consideration. Accordingly, the methods of this invention may be practiced under a variety of reaction conditions, as long as the monoclonal antibodies are not prevented from complexing with the reactant(s) or otherwise rendered inactive. More specifically, suitable conditions for complex formation encompass solution phase and emulsion reaction systems including a protic solvent, preferably water, maintained at a pH value between about 6.0 and about 8.0, preferably between about 6.0 and about 7.5, and at a temperature from about 4° C. to about 50° C., preferably from about 20° C. to about 45° C. The method of this invention may be carried out at reduced or elevated pressure, but preferably is practiced at ambient pressure. In addition to solution phase and emulsion reaction systems, suitable conditions also include the use of support materials to which the monoclonal antibody is attached. Such support materials are well-known to those of ordinary skill in the art as are methods for attaching monoclonal antibodies to them.

Example 11

Methyl 2,3,4-tri-O-benzyl-6-deoxy-β-D-gluco-heptodialdo-1.5-pyranoside.

A solution of oxalyl chloride (110 μl), 1.3 mmol) in dry dichloromethane (1.55 ml) was stirred under nitrogen atmosphere and cooled to −78° C. Dimethyl sulfoxide (0.178 ml, 2.5 mmol) in dichloromethane (0.67 ml) was added dropwise over 10 min. After stirring for 5 min methyl 2,3,4-tri-O-benzyl-6-deoxy-β-D-gluco-hepto-1,5-pyranoside (0.40 g, 0.8 mmol) dissolved in dichloromethane (0.67 ml) was added dropwise over 5 min. After stirring for another 15 min at −78° C., triethylamine (0.88 ml, 0.8 mmol) was added. The reaction mixture was allowed to warm to room temperature (30 min). Dichloromethane (1 ml) and water (4 ml) was added. The organic layer was extracted with water (4 ml) and brine (4 ml), dried (MgSO$_4$), filtered and concentrated. The residue was co-concentrated with toluene (2×3 ml) to give a colorless syrup in 93% (0.37 g) yield, $[\alpha]_D^{20}$=+18.07° (c 1.4, CHCl$_3$). $^{13}$C-NMR (CDCl$_3$):δ200 (C-7), 97.8 (C-1), 81.6, 80.7 and 79.9 (C-2, C-3, C-4); 75.5, 74.8 and 73.2 (3×CH$_2$OPh); 65.4 (C-5), 55.3 (OCH$_3$); 45.6 (C-6). Methyl 2,3,4-tri-O-benzyl-6,7-dideoxy-7-[(3R,4R,5R)-3-benzyloxy-4-hydroxy-5-hydroxymethl-piperidinyl]-α-D-gluco-heptopyranoside.

To a solution of methyl 2-3,4-tri-O-benzyl-6-deoxy-β-D-gluco-heptodialdo-1,5-pyranoside (0.961 g, 2.0 mmol) in ethanol (30 ml) was added (3R,4R,5R)-3-benzyloxy-4-hydroxy-5-hydroxymethylpiperidine (0.475 g, 2.0 mmol) dissolved in ethanol (30 ml) and 5% Pd/C (300 mg). The mixture was hydrogenated at 300 Psi and 20° C. for 66 h. The reaction mixture was filtered and concentrated. The resulting mixture was flash chromatographed using ethyl acetate and ethyl acetate/methanol 10:1 as eluent to give the product in 76% yield (1.06 g) $[\alpha]_D^{20}$=−2.9° (c 0.95, CHCl$_3$). MS (CC, NH$_3$): m/z 298 (M+H$^+$). $^{13}$C-NMR (CDCl$_3$):δ97.4 (C-1), 81.9, 81.8, 79.9, 79.8 and 75.5 (5×CH-OH); 76.4, 75.0, 73.0 and 71.6 (4×CH$_2$OPh), 67.8 (C-5), 64.5 (C-5'), 54.5, 54.3 and 53.8 (3×CH$_2$N and OCH$_3$), 42.6 (C-5'), 27 (C-6).
Methyl 6,7-dideoxy-7-[(3R,4R,5R)-3,4-dihydroxy-5-hydroxymethyl-piperidinyl]-α-D-gluco-heptopyranoside.

To a solution of methyl 2,3,4-tri-O-benzyl-6,7-dideoxy-7-[(3R,4R,5R)-3-benzyloxy-4-hydroxy-5-hydroxymethyl-piperdinyl]-α-D-gluco-heptopyranoside in ethanol (20 ml) was added 0.5M HCI (1.8 ml) and 5% Pd/C. The mixture was hydrogenated at 1 atm and 20° C. for 22 h. The reaction mixture was filtered and concentrated to give the product as a colorless syrup in 94% (203 mg) yield. $[\alpha]_D^{20}$=+36.71° (c 0.85; MeOH). $^{13}$C-NMR (D$_2$O):δ98.6 (C-1), 72.2 and 72.3 (C-3, C-4), 70 (C-2, C-4'), 68.0 (C-5), 67.9 (C-3'); 58.2 (C-5'), 54.6 (OCH$_3$), 54.0 (C-2'), 53.5 (C-7), 53.0 (C-6'), 40.3 (C-5'), 25.1 (C-6). $^1$H-NMR (D$_2$O):δ4.69 (d, 1H, H-1, J$_{1,2}$=3.7), 3.78 (dd, 1H, H-5''a, J$_{5''a,5''b}$=12, J$_{5',5a''}$=3.5 Hz), 3.77 (m, 1H, H-3'), 3.71 (dd, 1H, H-5''b, J$_{5''b,5'}$=6 Hz), 3.65 (m, 1H, H-2'eq), 3.62 (m, 1H, H-6'eq), 3.61 (m, 1H, H-5), 3.55 (m, 1H, H-4'), 3.53 (dd, H-2, J$_{2,3}$=10 Hz), 3.48 (dd, 1H, H-3, J$_{3,4}$=9 Hz), 3.33 (m, 1H, H-7a), 3.28 (m, 1H, H-7b), 3.23 (t, 1H, H-4, J$_{4,5}$=9 Hz), 2.98 (t, 1H H-6'ax, J$_{6'ax,6'eq}$=J$_{6'ax,5'}$=12.4 Hz), 2.88 (t, 1H, H-2'ax, J$_{2'ax,2'eq}$=J$_{2'ax,3'}$=11,9 Hz), 2.22 (m, 1H, H-6a), 1.96 (m, 2H, H-5' and H-6b).

Example 12

The disaccharide of Example 11, methyl 6,7-dideoxy-7-[(3R,4R,5R)-3,4-dihydroxy-5-hydroxymethyl-piperidinyl]-α-D-gluco-heptopyranoside, was dissolved in water and treated with hydrogen peroxide (50% weight solution). The mixture was stirred at room temperature until the reaction was complete. The solvent was then removed. 3 mg of methyl 6,7-dideoxy-7-[(3R,4R,5R)-3,4-dihydroxy-5-hydroxymethyl-piperidinyl]-α-D-gluco-heptopyranoside disaccharide nitrogen oxide was thus obtained, having a molecular weight of 353.369 g/mol.

All references cited in this application are hereby incorporated by reference as if individually incorporated by reference.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A compound of the formula

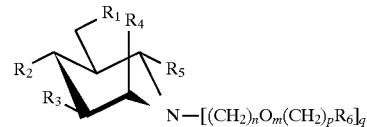

wherein n, m, and p, which may be the same or different, are a number between 0 and 5; q is a number between 0 and 10; R$_1$, R$_2$, R$_3$, R$_4$ and R$_5$, which may be the same or different, are a hydrogen, a hydroxyl, a halogen atom, a hydrocarbon or an O-hydrocarbon group having between 1 and 6 carbons which is aliphatic, alicyclic or aromatic, or a glycosyl group; and R$_6$ is a glycosyl group.

2. A compound according to claim 1 of the formula

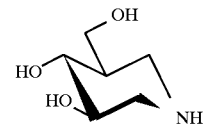

3. A compound according to claim 1 of the formula

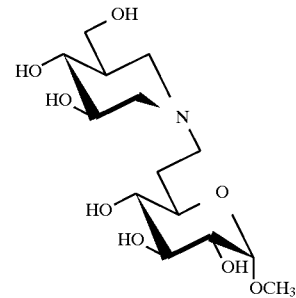

4. A pharmaceutical composition of matter comprising the compound of claim 1 in an amount effective for inhibiting glycosidase activity, and a pharmaceutically acceptable carrier therefor.

5. A treatment composition for cellulosic material comprising the compound of claim 1 in an amount effective for treating or inhibiting cellulase degradation in a cellulosic material.

6. A compound of the formula

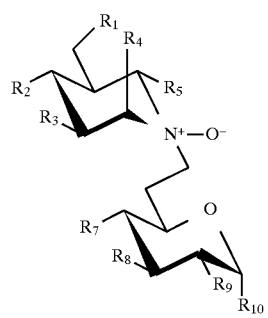

wherein $R_1$, $R_2$, $R_3$, $R_4$, $R_5$, $R_7$, $R_8$, $R_9$ and $R_{10}$, which may be the same or different, are a hydrogen, a hydroxyl, a halogen, a hydrocarbon or an O-hydrocarbon group having between 1 and 6 carbons which is aliphatic, alicyclic or aromatic, or a glycosyl group.

7. A compound according to claim 6 of the formula

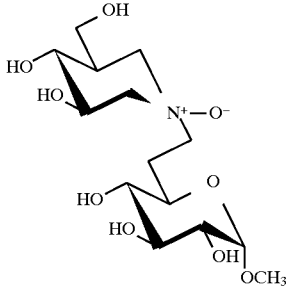

8. The compound of claim 1, wherein n and m, which may be the same or different, are a number between 0 and 4, and wherein n+m=4.

9. The compound of claim 1, wherein n, m, and p, which may be the same or different, are a number between 0 and 3.

10. The compound of claim 9, wherein n, m and p are each 2.

* * * * *